(12) United States Patent
Estes et al.

(10) Patent No.: US 12,403,257 B2
(45) Date of Patent: *Sep. 2, 2025

(54) INFUSION PUMP ASSEMBLY AND METHOD

(71) Applicant: INSULET CORPORATION, Acton, MA (US)

(72) Inventors: Mark C. Estes, Malibu, CA (US); Wenkang Qi, Cupertino, CA (US); David Thrower, San Jose, CA (US)

(73) Assignee: INSULET CORPORATION, Acton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/779,971

(22) Filed: Jul. 22, 2024

(65) Prior Publication Data

US 2024/0374822 A1 Nov. 14, 2024

Related U.S. Application Data

(63) Continuation of application No. 17/243,020, filed on Apr. 28, 2021, now Pat. No. 12,053,615, which is a
(Continued)

(51) Int. Cl.
| | |
|---|---|
| *A61M 5/172* | (2006.01) |
| *A61M 5/14* | (2006.01) |
| *A61M 5/142* | (2006.01) |
| *G16H 20/17* | (2018.01) |
| *G16H 40/63* | (2018.01) |

(Continued)

(52) U.S. Cl.
CPC ........ *A61M 5/1723* (2013.01); *A61M 5/1413* (2013.01); *A61M 5/14244* (2013.01); *G16H 20/17* (2018.01); *G16H 40/63* (2018.01);

*G16H 40/67* (2018.01); *G16Z 99/00* (2019.02); *A61M 2005/14208* (2013.01); *A61M 2205/332* (2013.01); *A61M 2205/3561* (2013.01); *A61M 2205/3569* (2013.01); *A61M 2205/3584* (2013.01); *A61M 2205/3592* (2013.01); *A61M 2205/50* (2013.01); *A61M 2205/502* (2013.01);
(Continued)

(58) Field of Classification Search
CPC .............. A61M 5/1413; A61M 5/1723; A61M 5/14244; A61M 5/14248; A61M 2230/005; A61M 2230/201; A61M 2005/142; A61M 2005/14208; A61M 2205/3592; G16H 40/63; G16H 40/67; G16H 20/17; A61B 5/14532

See application file for complete search history.

(56) References Cited

U.S. PATENT DOCUMENTS

| | | | |
|---|---|---|---|
| 2009/0069785 A1* | 3/2009 | Miller .................... | A61M 5/172 604/151 |
| 2010/0049164 A1* | 2/2010 | Estes ................. | A61M 5/14244 604/504 |

(Continued)

*Primary Examiner* — Jason E Flick
(74) *Attorney, Agent, or Firm* — Goodwin Procter LLP

(57) ABSTRACT

Some embodiments of an infusion pump assembly may be equipped with one or more components to facilitate wireless operation of an infusion pump via a user-operated mobile device. In some embodiments, the mobile device and/or the infusion pump may prompt the user to confirm acceptance of a wirelessly communicated command to prevent an operation by the infusion pump (e.g., a dispensation of medicine) that is not desired by the user.

20 Claims, 12 Drawing Sheets

Related U.S. Application Data continuation of application No. 16/168,148, filed on Oct. 23, 2018, now Pat. No. 10,994,078, which is a continuation of application No. 14/453,596, filed on Aug. 6, 2014, now Pat. No. 10,137,246.

(51) Int. Cl.
*G16H 40/67* (2018.01)
*G16Z 99/00* (2019.01)

(52) U.S. Cl.
CPC ... *A61M 2205/52* (2013.01); *A61M 2230/005* (2013.01); *A61M 2230/201* (2013.01)

(56) References Cited

U.S. PATENT DOCUMENTS

| | | | |
|---|---|---|---|
| 2011/0144616 A1* | 6/2011 | Michaud | F04B 53/143 604/153 |
| 2014/0113553 A1* | 4/2014 | Brukalo | G16H 40/67 455/41.1 |
| 2015/0025498 A1* | 1/2015 | Estes | G16H 10/60 604/151 |
| 2016/0067417 A1* | 3/2016 | Bayer | A61M 5/31553 604/208 |

* cited by examiner

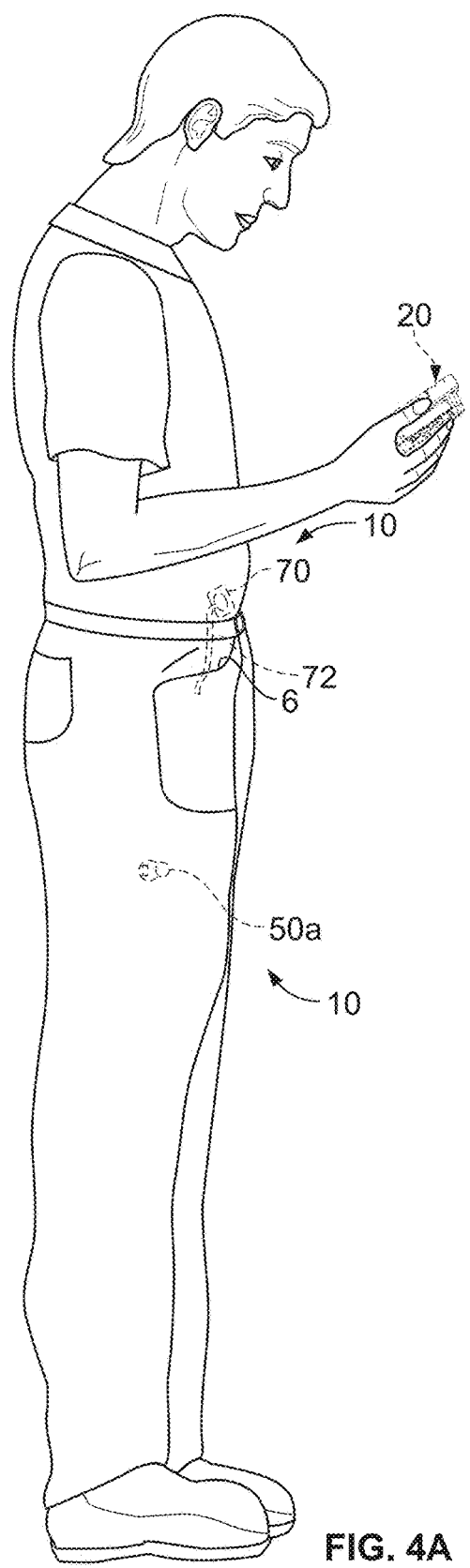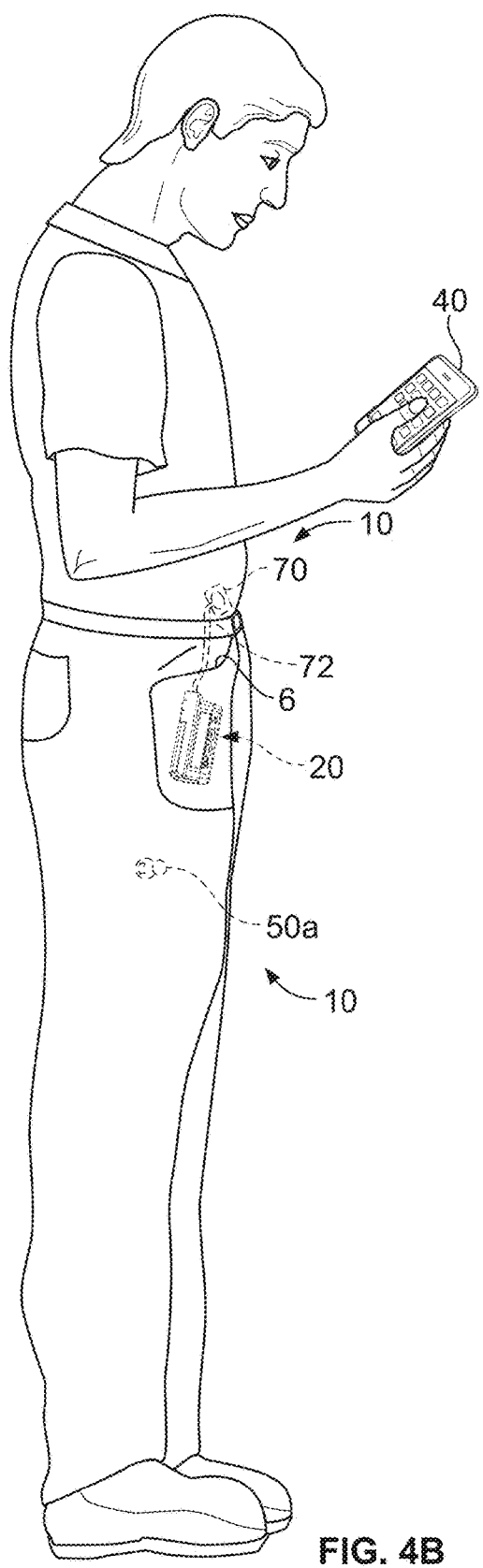
FIG. 4A
FIG. 4B

INFUSION PUMP ASSEMBLY AND METHOD

CROSS-REFERENCE TO RELATED APPLICATIONS

This application is a continuation application of U.S. application Ser. No. 17/243,020, filed on Apr. 28, 2021, which is a continuation application of U.S. application Ser. No. 16/168,148 (now U.S. Pat. No. 10,994,078), filed on Oct. 23, 2018, which is a continuation application of and claims priority to U.S. application Ser. No. 14/453,596 (now U.S. Pat. No. 10,137,246), filed on Aug. 6, 2014. The disclosures of the prior applications are considered part of the disclosure of this application, and are incorporated in their entirety into this application.

TECHNICAL FIELD

This document relates to an infusion pump assembly, such as a portable infusion pump assembly for dispensing a medicine.

BACKGROUND

Pump systems are commonly used to deliver one or more fluids to a targeted individual. For example, a medical infusion pump system may be used to deliver a medicine to a patient as part of a medical treatment. The medicine that is delivered by the infusion pump system can depend on the condition of the patient and the desired treatment plan. For example, infusion pump systems have been used to deliver insulin to the vasculature of diabetes patients so as to regulate blood-glucose levels.

Users of infusion pump devices often need to communicate with the infusion pump via a user interface to control the operations of the infusion pump in a safe and effective manner. For example, a user may press a series of buttons on the user interface to enter food intake data into the infusion pump, such as a number of grams of carbohydrates that is indicative of a recently or soon-to-be consumed meal. The food intake data can be combined by the infusion pump assembly with other parameters to calculate a suggested dosage of insulin based on the grams of carbohydrates entered by the user. In another example, a user may enter information into the infusion pump assembly via a user interface that indicates that the user is going to perform a level of physical exercise. In some circumstances, the infusion pump system may reduce the amount of a planned dispensation of insulin in response to the exercise information entered by the user.

In some systems, a wireless remote controller is provided to facilitate wireless and operation of an infusion pump assembly. Wireless remote control of the pump assembly, however, introduces two primary concerns regarding patient safety: 1) A concern that a third-party could control the pump assembly by hijacking the wireless connection between the pump assembly and the remote controller; and 2) A concern that a virus, programming error, or a third-party application interfering with the remote controller could adversely affect operation of the pump assembly.

SUMMARY

Some embodiments of an infusion pump system may be equipped with one or more components to facilitate wireless communication between a mobile communication device and an infusion pump assembly. In some embodiments, the mobile device (e.g., a smartphone) can wirelessly transfer data to the infusion pump assembly that may cause the pump assembly to execute a particular sequence of operations (e.g., operations to provide a controlled dispensation of medicine). In particular, the mobile device may communicate one or more user input commands to the infusion pump assembly (e.g., user input commands that might otherwise be input via a series of menu selections and data entry steps on the user interface of the infusion pump assembly) to initiate a suggested bolus dosage of insulin (or another medication). In some embodiments, the smartphone device is operable to execute a dosage calculator application that determines the suggested bolus dosage based on information indicative of the user's blood glucose level. In some embodiments, the smartphone device and/or the infusion pump assembly may prompt the user to confirm acceptance of the suggested bolus dosage to prevent a dispensation of medicine that is not desired by the user.

Particular embodiments described herein provide a medical infusion pump system including a portable pump housing configured to receive insulin for dispensation to a user, a controller communicatively coupled with the pump drive system, and a wireless communication device configured to receive a suggested dosage amount from a mobile device. The pump housing may at least partially contain a pump drive system to dispense the insulin through a flow path to the user, and the controller can be operable to cause controlled dispensation of the insulin from the portable pump housing by the pump drive system. In some embodiments, the controller may, in response to receiving the suggested dosage amount from the mobile device, prompt the user for confirmation of acceptance of the suggested dosage.

In some optional aspects, the system may further include the mobile device, and the mobile device may include a memory device that stores a mobile application configured to receive blood glucose information of the user and food consumption information of the user. The mobile device may be a smartphone device. The controller may be configured to prompt the user for confirmation of acceptance of the suggested bolus dosage by transmitting a confirmation signal to the mobile device indicating receipt of the suggested dosage amount to cause the mobile device to prompt the user to provide at least one of a security code and a biometric validation to confirm acceptance of the suggested bolus dosage. The system may further include a glucose monitoring device configured to be worn by the user and configured to wirelessly communicate blood glucose information of the user. The system may further include a blood strip reader device configured to determine a blood glucose level of the user. The blood strip reader device may be configured to wirelessly communicate blood glucose information of the user.

Other embodiments described herein provide a method that includes receiving input via wireless communication from a mobile device, such as smartphone device, that is indicative of a task to be performed by a portable infusion pump system. The may also include prompting a user to confirm, via interaction with the portable infusion pump system, a change in operation of the portable infusion pump system according to the input received from the smartphone device.

In some optional aspects, the method may further include activating the change in operation of the portable infusion pump system in response to the user's confirmation via interaction with the portable infusion pump system. The user's confirmation via interaction with the portable infusion pump system may include bumping the smartphone device in proximity to the portable infusion pump system such that both the smartphone device and the portable infusion pump system detect a bump motion. The user's confirmation via interaction with the portable infusion pump system may include input via a touchscreen or button of the portable infusion pump system. The method may also optionally include rejecting the change in operation of the portable infusion pump system after lapse of a predetermined period of time in which no use confirmation is received. The method may further include rejecting the change in operation of the portable infusion pump system after receiving input from the user, via interaction with the portable infusion pump system, indicative of a rejection of the change in operation. The input received from the smartphone device may include information indicative of a calculated bolus dosage. The input received from the smartphone device may include information indicative of a temporary basal rate. The smartphone device may execute a mobile application configured to output a suggested change in operation of the portable infusion pump.

In some embodiments described herein, a system may include a smartphone device including a memory device (e.g., a RAM memory module, another computer-readable memory device, or the like) storing computer-readable instructions that cause the smartphone to access a dosage calculator application, and a wireless communication device of the smartphone device configured to wirelessly communicate with a portable infusion pump system. Optionally, the dosage calculator application is configured to calculate a suggested bolus dosage that is wirelessly communicated to the portable infusion pump system, and the smartphone device wirelessly receives information indicative of a user's confirmation of the suggested bolus dosage.

In some optional aspects, the system may further include the portable infusion pump system, and the portable infusion pump system may be configured to prompt the user for confirmation of acceptance of the suggested bolus dosage. The system may also optionally include a glucose monitoring device configured to be worn by the user and configured to wirelessly communicate blood glucose information of the user to the smartphone device. The system may optionally include a blood strip reader device configured to determine a blood glucose level of the user and configured to wirelessly communicate blood glucose information of the user to the smartphone device.

In some embodiments described herein, a medical infusion pump system may include a portable pump housing configured to receive insulin for dispensation to a user. The system may also include a controller communicatively coupled with the pump drive system. Also, the system may include a mobile device communicatively coupled with the controller to provide a trigger signal via a wireless connection to initiate dispensation of the insulin according to a bolus dosage. The pump housing at least partially contains a pump drive system to dispense the insulin through a flow path to the user, and the controller is operable to cause controlled dispensation of the insulin from the portable pump housing by the pump drive system. In some circumstances, in response to receiving the trigger signal, the controller prompts the user for confirmation of acceptance of the bolus dosage.

In some embodiments described herein, a method may include receiving input from a mobile device that is indicative of a task to be performed by a portable infusion pump system. The method may further include receiving, via near field communication (NFC) from a NFC device (e.g., an NFC tag or an NFC circuit) incorporated in the mobile device, a signal indicative of a user's confirmation of acceptance of a change in operation of the portable infusion pump system according to the input received from the mobile device. The method may also include, in response to receiving the signal, controlling the portable infusion pump system according to the user-confirmed change in operation.

In other embodiments described herein, a method may include transmitting input via wireless communication from a smartphone device that is indicative of a task to be performed by a portable infusion pump system. The method may also include prompting a user to confirm, via interaction with the smartphone device, a change in operation of the portable infusion pump system according to the input transmitted from the smartphone device.

Some or all of the embodiments described herein may provide one or more of the following advantages. First, some embodiments of the infusion pump system may be configured to send and receive data communications wirelessly using NFC and/or short-range wireless communication technology implemented on a mobile device and an infusion pump assembly, thereby providing convenient wireless communications while also reducing the likelihood of long-range hijacking of the wireless communications to the infusion pump assembly. Second, some embodiments of an infusion pump system may provide safe and reliable wireless control of an infusion pump assembly by a mobile device. Third, some embodiments of the infusion pump system may facilitate user confirmation of a pump-assembly operation initiated wirelessly via the mobile device to prevent such operations that are unintended by the user. Fourth, some embodiments of an infusion pump system may facilitate convenient user input of information to the infusion pump assembly via a smartphone operated by the user. Fifth, some embodiments of an infusion pump system equipped with wireless communication capabilities may be configured to be portable, wearable, and (in some circumstances) concealable. For example, a user can conveniently wear one or more components of the infusion pump system on the user's skin under clothing or can carry such components in the user's pocket (or other portable location) while receiving medicine dispensed from an infusion pump device. Sixth, in some embodiments of an infusion pump system, the user can wirelessly operate an infusion pump assembly without removing the pump assembly from a portable and concealed location. Seventh, in some embodiments of an infusion pump system, a mobile device configured to wirelessly operate the infusion pump assembly can include a dosage calculator software application that accurately calculates a suggested bolus dosage based on data indicative the user's blood glucose level. Eight, in some embodiments of the infusion pump system, the software application may utilize the bolus calculation feature in combination with a glucose monitoring device and/or a blood glucose test strip reader that wirelessly transmits blood glucose information to the mobile device.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4A-C are a side views of the infusion pump system of FIGS. 2A-B in which the infusion pump assembly is worn on clothing of a user and operated wirelessly in accordance with particular embodiments.

DETAILED DESCRIPTION OF ILLUSTRATIVE EMBODIMENTS

Figure 1:
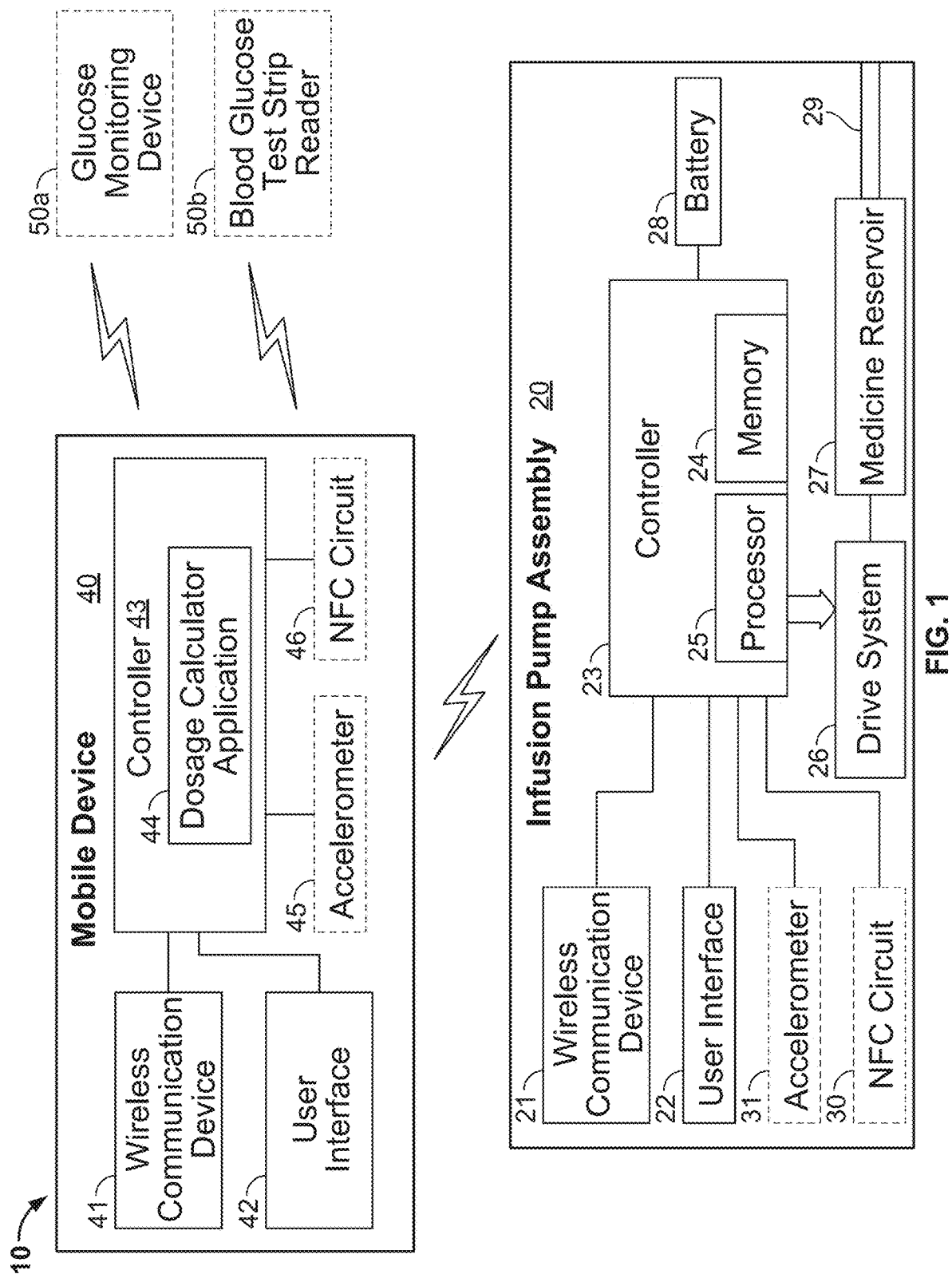
FIG. 1 is a block diagram of an infusion pump system in accordance with some embodiments.

Referring to FIG. 1, an infusion pump system 10 can include an infusion pump assembly 20 and a mobile device 40, such as a smartphone device configured to connect with the internet and to execute mobile applications. The pump assembly 20 and the mobile device 40 are communicatively coupled to one another. The pump assembly 20 is configured to controllably dispense dosages of medicine to be infused into the tissue or vasculature of a targeted individual, such as a human or animal patient. For example, as described below, the infusion pump assembly 20 can be used to deliver insulin or another medicinal fluid for purposes of regulating the user's blood glucose levels. However, numerous other types of medicines can be used in some embodiments, including: pain relief drugs, hormone therapy, blood pressure treatments, anti-emetics, osteoporosis treatments, or other injectable medicines. As described below, the mobile device 40 can wirelessly communicate (e.g., via near field communication (NFC), Bluetooth connectivity, or another short-range wireless connection, or via radio frequency (RF) or Wi-Fi connectivity, or another wireless connection) with the pump assembly 20 to facilitate remote control of the pump assembly 20 by a user operating the mobile device 40.

In this embodiment, the pump assembly 20 includes a wireless communication device 21, a user interface 22, and a controller 23. The wireless communication device 21 is operable to send and receive data signals (e.g., discrete data packets or a continuous data stream) to and from a corresponding wireless communication device 41 of the mobile device 40. For example, the wireless communication device 21 may receive a trigger signal from the wireless communications device 41 of the mobile device 40 to initiate a suggested dosage of medicine. The user interface 22 can be engaged by a user to control the operation of the pump assembly 20. For example, in some embodiments, the user can engage the user interface 22 to confirm acceptance, decline acceptance, or modify a dosage of medicine suggested by the mobile device 40.

The controller 23 is operable to generate control signals that are transmitted to various other components of the pump assembly 20, and to receive feedback signals from one or more of those components. The controller 23 includes a memory 24 that stores data and computer-readable instructions for processing/execution by a processor 25. The processor 25 receives program instructions and feedback data from the memory 24, executes logical operations called for by the program instructions, and generates command signals for operating the various components of the pump assembly 20. For example, the controller 23 can cause a suggested dosage received by the wireless communication device 21 to be presented to the user via the user interface 22 (e.g., by display or audible speech output). Further, the controller 23 can cause a drive system 26 of the pump assembly 20 to dispense the suggested dosage of medicine from the medicine reservoir 27. The controller is electrically powered by a battery 28.

In some embodiments, the medicine reservoir 27 can be provided in the form of a pre-filled cartridge slidably received within a housing of the pump assembly 20. In such embodiments, the drive system 26 can advance a plunger into the reservoir 27 so as to dispense medicine therefrom, which causes the medicine to be dispensed through tubing 29 of an infusion set. As described in more detail below, the medicine reservoir 27 can be received within a cavity in the infusion pump assembly 20. In some embodiments, the reservoir 27 is a replaceable reservoir such that, when the replaceable reservoir is exhausted, the replaceable reservoir can be removed from the infusion pump assembly 20 and replaced with another new pre-filled reservoir. In other embodiments, the reservoir 27 may be non-removably received in the pump assembly 20 such that, when the medicine reservoir 27 is exhausted, the portion of the pump assembly 20 that retains reservoir 27 is discarded along with the reservoir 27 (refer, for example, to FIG. 2). For example, as described in more detail below, the infusion pump assembly 20 may optionally comprise multiple readily detachable portions, with various components of the infusion pump assembly 20 residing in different detachable portions. In one example described in FIG. 2 below, at least the controller 23, the user interface 22, and the wireless communication device 21 can be contained within a first (reusable) detachable portion while the drive system 26, and the medicine reservoir 27 are contained within a second (disposable, single-use) detachable portion.

In some optional embodiments, the pump assembly 20 may further include a NFC circuit 30 responsive to an optional NFC circuit 46 incorporated in the mobile device 40. NFC provides particularly short-range wireless communication. In some embodiments, the maximum working distance for NFC is less than 12 inches, about 8 inches or less, and about 4 inches or less. NFC allows sharing of relatively small packets of data between devices equipped with NFC functionality. In some embodiments, wireless NFC data transmission can be a two-way wireless communication. In other words, two interfacing NFC circuits can pass data packets back and forth between one another. The data communicated via NFC can be written in a variety of formats. One example format is called the NFC Data Exchange Format ("NDEF"). The NFC circuit 30 of the pump assembly 20 can be implemented as a separate structure from the wireless communication device 21, or can be implemented as part of the wireless communication device 21. Likewise, the NFC circuit 46 of the mobile communications device 40 can be implemented as a separate structure from the wireless communication device 41, or can be implemented as part of the wireless communication device 41.

Further, although one or more embodiments described herein involve NFC communication via two intercommunicating NFC circuits, various other embodiments may incorporate one or more NFC tags. For example, the NFC circuit 46 of the mobile device could be replaced by an NFC tag. An NFC tag can store about a kilobyte of data or less, although NFC tags that store a greater quantity of data can also be used in the embodiments described herein. The NFC tags can be configured with a shape that is small and lightweight (e.g., a maximum dimension of about 1 inch or less), particular because the NFC tags described the embodiment of FIG. 1 do not have an integral power source such as a battery. Instead, a coil in the NFC tag inductively receives magnetic field energy that is emitted from a coil in NFC circuit housed in the portable infusion pump 66. Accordingly, energy and data can be wirelessly transmitted between the coils of the NCF tag and the device with NFC functionality.

Figure 4C:
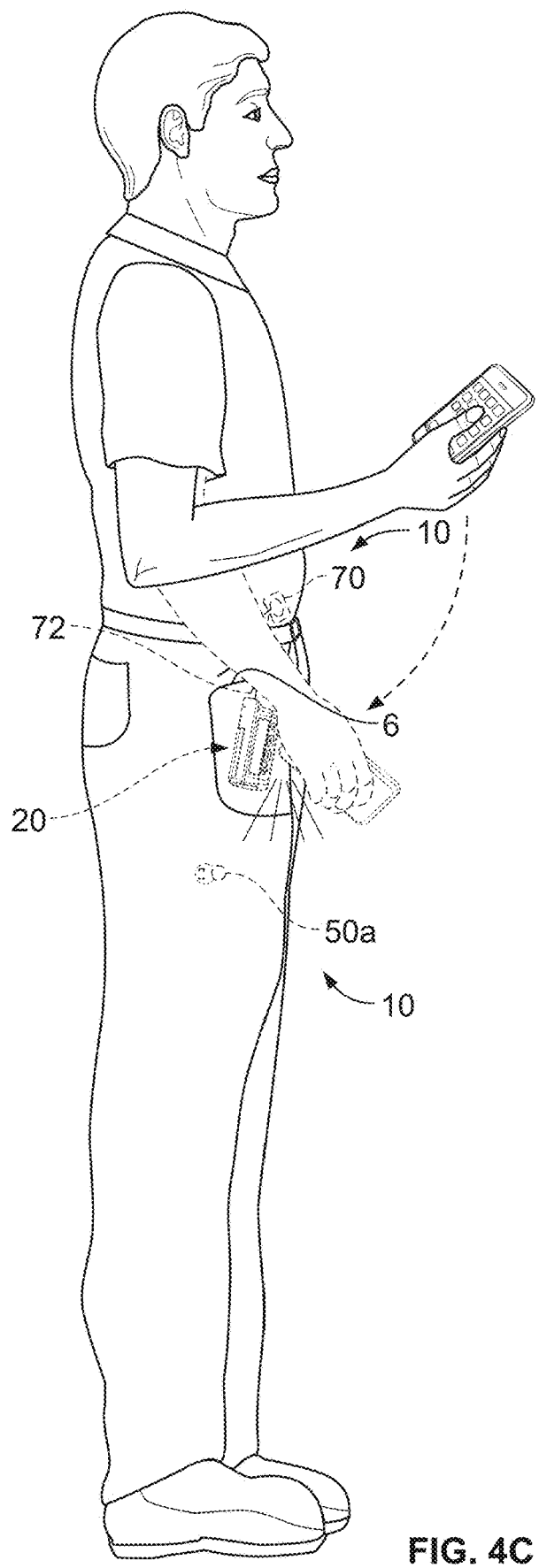

The NFC circuits 30 and 46 may facilitate particularly short-range wireless communications between the pump assembly 20 and the mobile device 40 when the NFC circuits 30 and 46 are in a NFC proximity range. The NFC circuit 30 can be electrically connected with the controller 23 to transfer data communicated by the corresponding NFC circuit 46 of the mobile device 40 to the controller 23. The NFC proximity range may be preferably within a range four inches or less, including for example, a physical "bump" between the pump assembly 20 and the mobile device 40. In some embodiments, the NFC circuit 30 can communicate data to the controller 23 indicating that the user has confirmed acceptance of a suggested medicine dosage provided by the mobile device 40. For example, as described in detail below, the user can bump the mobile device 40 against the pump assembly 20 to confirm that the suggested medicine dosage is accepted by the user and therefore should be dispensed (FIGS. 4C and 6B).

In some optional embodiments, the pump assembly 20 may include at least one accelerometer 31 electrically connected with the controller 23. In some embodiments, feedback from the accelerometer 31 (or from a set of accelerometers) can be used by the controller 23 to execute NFC communications when accelerated movement at or above the threshold level is detected. Further in some embodiments, the controller 23 can utilize movement information provided by the accelerometer 31 as independent detection of a bump between the pump assembly 20 and the mobile device 40.

The mobile device 40 includes the wireless communications device 41, the NFC circuit 46, or both so as to facilitate communications with the pump assembly 20 (as described above) and a user interface 42 to facilitate user operation of the mobile device 40. The wireless communications device 41 and the user interface 42 are electronically coupled to a controller 43 that controls and receives feedback data from the various components (including the accelerometer 45 and the NFC circuit 46) of the mobile device 40. As noted above, the mobile device 40 can facilitate remote operation of the pump assembly 20. For example, a user can input an insulin dosage (e.g., a bolus dosage or a temporary basal rate dosage) to the controller 43 via the user interface 42, and the controller 43 can cause the wireless communications device 41 to transmit a data signal including the suggested dosage to the pump assembly 20. As shown, the controller 43 includes a dosage calculator application 44 provided in the form of computer-readable software program instructions configured, in this example, to calculate a suggested dosage of medicine based upon data related to the user's blood glucose level. The calculated dosage can also be communicated wirelessly to the pump assembly 20 (refer, for example, to FIG. 6).

In some embodiments, the infusion pump system 10 may optionally include a glucose monitoring device 50a and/or a blood glucose test strip reader 50b that communicate(s) with the mobile device 40 (e.g., via the wireless communication device 41) for the purpose of supplying data indicative of a user's blood glucose level to the controller 43. As noted above, the dosage calculator application 44 can utilize the data indicative of a user's blood glucose level in the calculation of a dosage. For example, the dosage calculator application 44 can calculate the recent rate of change in the user's blood glucose level and can use this rate-of-change information as a parameter in the calculation of a suggested bolus dosage of insulin (or another medication) for the user.

In some embodiments, the dosage calculator application 44 can be configured to determine basal rate dosages of insulin (or another medication) along with user-initiated bolus dosages. The basal delivery rate can be determined so as to maintain a user's blood glucose level in a targeted range during normal activity when the user is not consuming food items. The user-selected bolus deliveries may provide substantially larger amounts of insulin in particular circumstances in which the user's blood glucose level requires a significant correction or when the user has recently consumed (or is about to consume) food items. In some embodiments, the dosage calculator application 44 can determine a bolus dosage for the user in a manner that accounts for some of all of: the user's food intake, the user's recent blood glucose level (e.g., input by the user via the user interface 42, or received from the glucose monitoring device 50a or the blood glucose test strip reader 50b), the rate of change in the user's blood glucose level, and previously delivered insulin that has not acted on the user. For example, a user can enter a carbohydrate value indicative of a meal into the mobile device 40 via the user interface 42, and in response thereto, the dosage calculator application 44 can calculate a suggested bolus dosage, which is wireless communicated to the infusion pump assembly 20 (which then awaits confirmation from the user for purposes of additional security and accuracy).

For example, when a suggested dosage of medicine is calculated by the dosage calculator application 44, the controller 43 can cause the suggested dosage to be communicated to the pump assembly 20 by the wireless communication device 41 (or by the NFC communication circuit 46). The wireless communication device 21 (or the NCF circuit 30) of the pump assembly 20 can receive information indicative of the suggested dosage, and the controller 23 can cause the suggested dosage to be presented to the user via the user interface 22, with a prompt for the user to accept or reject the dosage amount for dispensation. If the user accepts the recommended dosage, the controller 23 can generate control signals to cause the drive system 26 to dispense the suggested dosage of glucagon from the medicine cartridge 27. If the user rejects the recommended dosage, the controller 23 can provide the user with an option to modify the dosage amount to a value different from the suggested dosage or to reject any bolus dosage at the present time.

Figure 2:
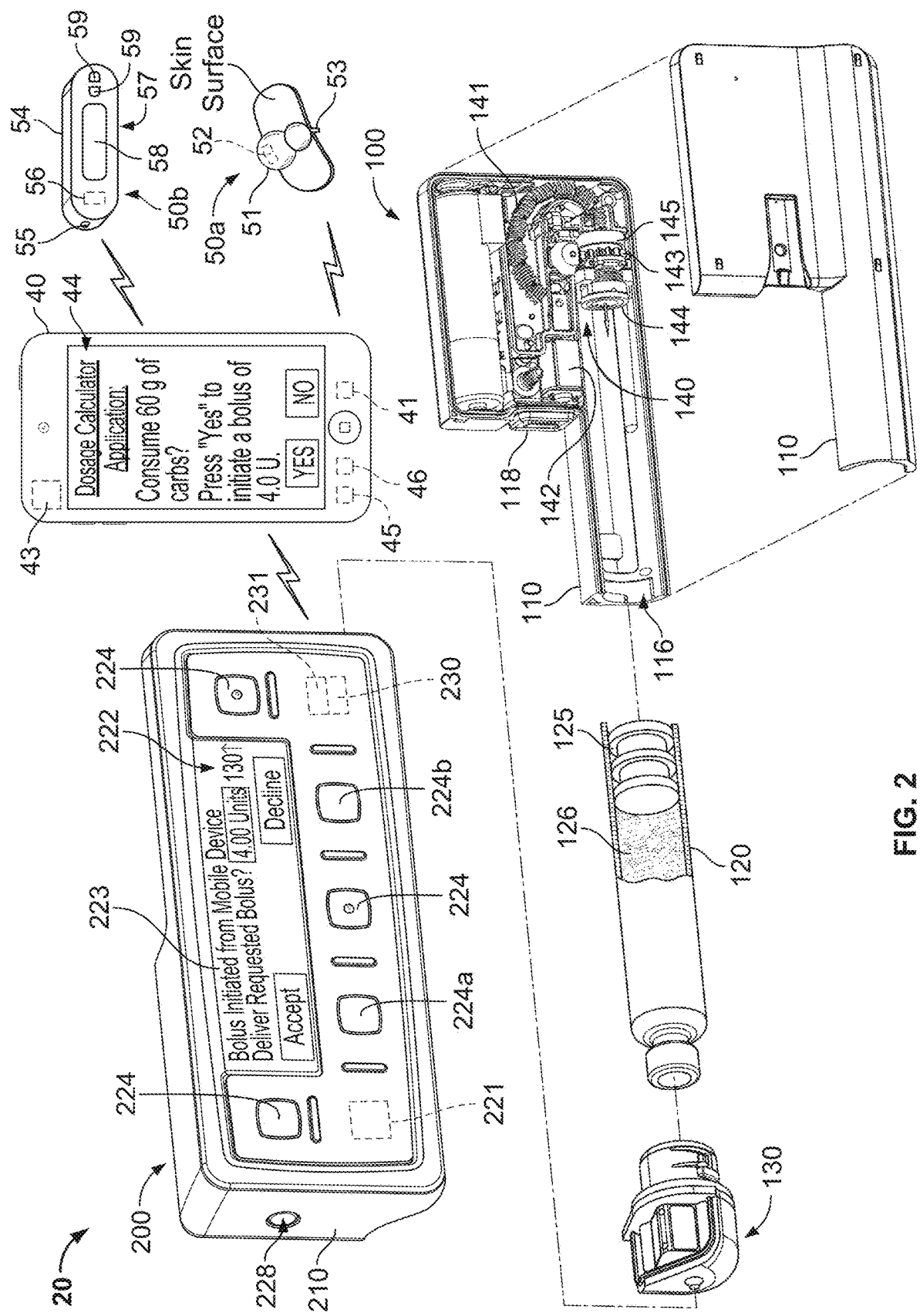
FIG. 2 is a schematic diagram of an infusion pump system including a perspective exploded view of an infusion pump assembly in accordance with some embodiments.
Figure 3:
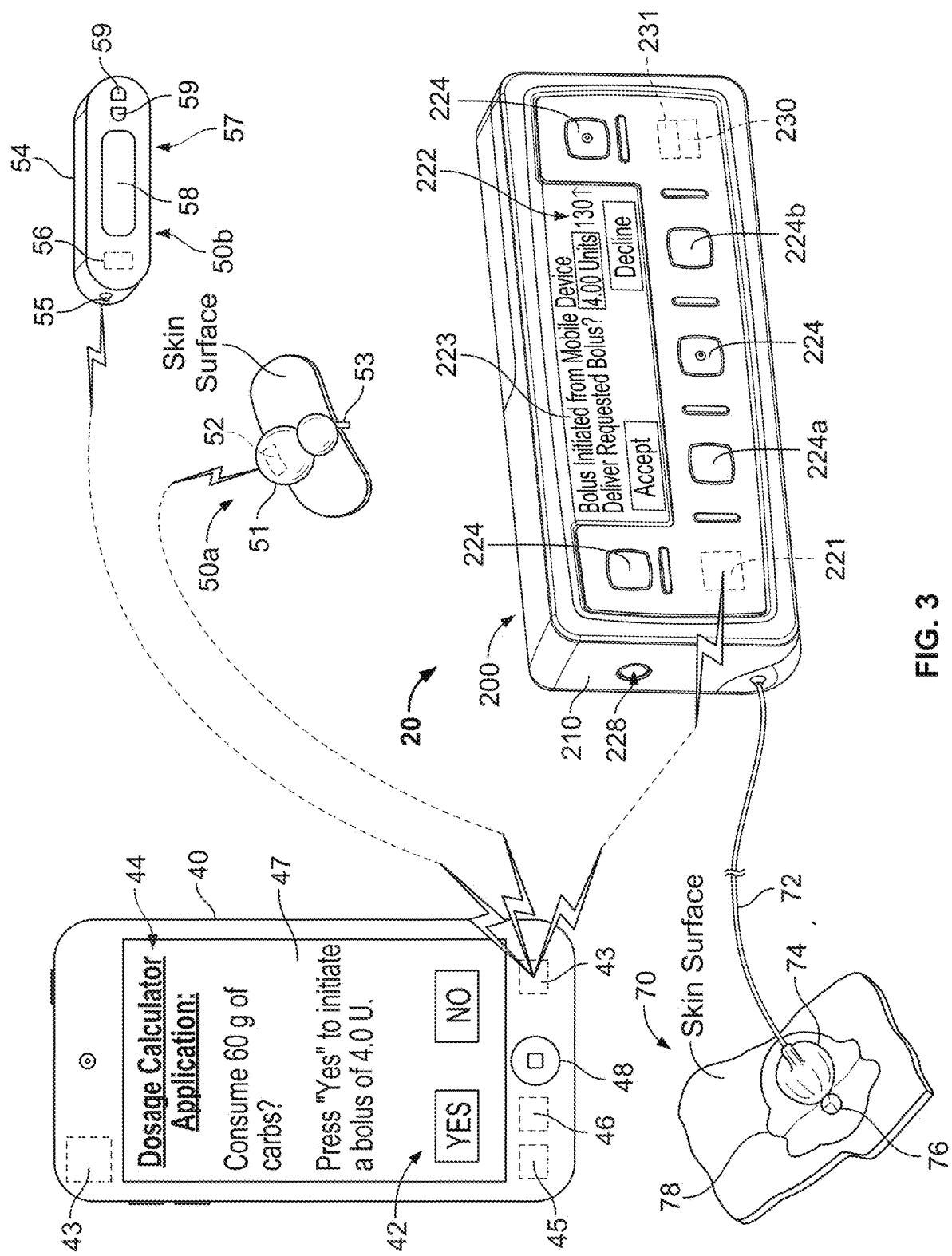
FIG. 3 is a schematic diagram of the infusion pump system including a perspective assembled view of the infusion pump assembly in accordance with some embodiments.

Referring now to FIGS. 2-3, some embodiments of the infusion pump assembly 20 includes a pump device 100 and a removably attachable controller device 200 that are used together for purposes of supplying insulin or another medication to a user. Also, in this embodiment of the system 10, the mobile device 40 is provided in the form of a smartphone device configured to connect with the internet and to execute mobile applications. As described above with reference to FIG. 1, the smartphone device 40 receives data indicative of a user's blood glucose level from the glucose monitoring device 50a and the blood glucose test strip reader 50b. In this embodiment, the smartphone device 40 is depicted as executing an example implementation of the dosage calculator application 44 (FIG. 1) that utilizes the data indicative of a user's blood glucose level in the calculation of a dosage.

Similar to the embodiment of FIG. 1, the smartphone device 40 includes the wireless communication device 41 and the controller 43 executing the dosage calculator application 44. The smartphone device 40 further includes at least one accelerometer 45 and the NFC circuit 46. In this embodiment, the user interface 42 of the smartphone 40 includes a touchscreen 47 and at least one button 48, and the user interface 42 is configured to allow a user to remotely control the infusion pump assembly 20. As described below, the user interface 42 may include various other components, e.g., one or more biometric recognition sensors and/or face recognition hardware). In various alternative embodiments, the mobile device 40 can be other types of devices such as a tablet computer, laptop computer, a PDA, a custom remote device manufactured specifically for interfacing with the pump assembly 20, and the like.

Still referring to FIGS. 2-3, the glucose monitoring device 50a can include a housing 51, a wireless communication device 52, and a sensor element 53. The wireless communication device 52 can be contained within the housing 51 and the sensor element 53 can extend outward from the housing 51. In use, the sensor element 53 can penetrate the skin surface of a user to make measurements indicative of characteristics of the user's blood (e.g., the user's blood glucose level or the like). In some embodiments, the glucose monitoring device 50a can include one or more electronic circuits that permit sensor signals (e.g., data from the sensor element 53) to be communicated to the communication device 52. Thus, in response to the measurements made by the sensor element 53, the glucose monitoring device 50a can employ the wireless communication device 52 to transmit data to the mobile device 40 via its wireless communication device 41.

In some embodiments, the monitoring device 50a can employ other methods of obtaining information indicative of a user's blood characteristics. For example, an alternative monitoring device may employ a micropore system in which a laser porator creates tiny holes in the uppermost layer of a user's skin, through which interstitial glucose is measured using a patch. Alternatively, the monitoring device can use iontophoretic methods to non-invasively extract interstitial glucose for measurement. In other examples, the monitoring device can include non-invasive detection systems that employ near IR, ultrasound or spectroscopy, and particular embodiments of glucose-sensing contact lenses. Invasive methods involving optical means of measuring glucose could also be added. In yet another example, the monitoring device can include an optical detection instrument that is inserted through the skin for measuring the user's glucose level.

The blood glucose test strip reader 50b can include a housing 54, a wireless communication device 55, a test-strip port 56, and a user interface 57 including a display 58 and user-selectable buttons 59. In use, a user can deposit a test strip carrying a blood sample into the test-strip port 56. The blood glucose test strip reader 50b can analyze the test strip and present data indicative of characteristics of the user's blood (e.g., the user's blood glucose level or the like) on the display 58. In some embodiments, the blood glucose test strip reader 50b can include one or more electronic circuits that permit sensor signals (e.g., data from the test-strip port 56) to be communicated to the communication device 55. Thus, using the user-selectable buttons 59, the user can cause the wireless communication device 55 to transmit the data to the mobile device 40 via its wireless communication device 41.

It should be understood that in some alternative embodiments, the glucose monitoring device 50a and the blood glucose test strip reader 50b may be operable to communicate data indicative of characteristics of the user's blood by a wired connection. Further, in some embodiments, such data can be entered directly into the mobile device 40 via the user interface 42.

In some embodiments, the controller device 200 of the infusion pump assembly 20 is equipped with wireless communication capabilities, and the controller device 200 is configured to mechanically mount together with the removable pump device 100 (exploded view shown in FIG. 2) so as to electrically communicate with the pump device 100. The pump device 100 in this embodiment includes a housing structure 110 that defines a cavity 116 in which a fluid cartridge 120 can be received. The pump device 100 can also include a cap device 130 to retain the fluid cartridge 120 in the cavity 116 of the housing structure 110. The pump device 100 can include a drive system 140 that advances a plunger 125 in the fluid cartridge 120 so as to dispense fluid 126 therefrom. In some embodiments, the dispensed fluid exits the fluid cartridge, passes through a flexible tube 72 of an infusion set 70 to a cannula housing 74 retained to the user's skin by a skin adhesive patch 78 (FIG. 3). The dispensed fluid can enter through the skin via a cannula 76 attached to the underside of the cannula housing 74 (FIG. 3).

In some embodiments, the controller device 200 communicates with the pump device 100 to control the operation of the drive system 140. When the controller device 200, the pump device 100 (including the cap device 130), and the fluid cartridge 120 are assembled together, the user can (in some embodiments) conveniently wear the infusion pump assembly 20 on the user's skin under clothing, in a pouch clipped at the waist (e.g., similar to a cell phone pouch), or in the user's pocket while receiving the fluid dispensed from the pump device 100 (see FIGS. 4A-C). Optionally, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted, and the pump device 100 can be equipped with one or more structures that physically hinder reuse of the pump device 100 with a subsequent cartridge 120 (e.g., such as one or more anchors that penetrate and retain the medicine cartridge 120 to hinder removal, the cap device 130 being non-reversibly attached to the pump housing 110, or the like). Thereafter, the user can removably attach a new pump device 100 (having a new medicine cartridge 120) to the reusable controller device 200 for the dispensation of fluid from a new fluid cartridge 120. Accordingly, the user is permitted to reuse the controller device 200 (which may include complex or valuable electronics, as well as a rechargeable battery) while disposing of the relatively low-cost pump device 100 after each use. Such a pump assembly 20 can provide enhanced user safety as a new pump device 100 (and drive system therein) is employed with each new fluid cartridge 120.

Briefly, in use, the pump device 100 is configured to removably attach to the controller device 200 in a manner that provides a secure fitting, an overall compact size, and a reliable electrical connection that can be resistant to water migration. For example, the controller device 200 can include a housing 210 having a number of features that mate with complementary features of the pump housing structure 110. In such circumstances, the controller device 200 can removably attach with the pump device 100 in a generally side-by-side configuration. The compact size permits the infusion pump assembly 20 to be discrete and portable. Moreover, at least one of the pump device 100 or the controller device 200 can include a release member that facilitates an easy-to-use detachment and replacement process.

As shown in FIG. 2, the pump device 100 can include an electrical connector 118 (e.g., having conductive pads, pins, and the like) that is exposed to the controller device 200 and that mates with a complementary electrical connector (not shown) on the adjacent face of the controller device 200. The electrical connection between the pump device 100 and the controller device 200 provides the electrical communication between the control circuitry housed in the controller device 200 and at least a portion of the drive system 140 or other components of the pump device 100. For example, in some embodiments, the electrical connection between the pump device 100 and the controller device 200 can permit the transmission of electrical control signals to the pump device 100 and the reception of feedback signals (e.g., sensor signals) from particular components within the pump device 100. The electrical connection between the pump device 100 and the controller device 200 may similarly facilitate transmission of one or more power signals for sharing electrical power therebetween.

The pump device 100 may include a drive system 140 that is controlled by the removable controller device 200. Accordingly, the drive system 140 can accurately and incrementally dispense fluid from the pump device 100 in a controlled manner. The drive system 140 may include a flexible piston rod 141 that is incrementally advanced toward the medicine cartridge 120 so as to dispense the medicine from the pump device 100. At least a portion of the drive system 140 is mounted, in this embodiment, to the pump housing structure 110. In some embodiments, the drive system 140 may include a number of components, such as an electrically powered actuator (e.g., reversible motor 142 or the like), a drive wheel 143, a bearing 145, the flexible piston rod 141, and a plunger engagement device 144. In this embodiment, the reversible motor 142 drives a gear system to cause the rotation of the drive wheel 143 that is coupled with the bearing 145. The drive wheel 143 may include a central aperture with an internal thread pattern, which mates with an external thread pattern on the flexible piston rod 141. The interface of the threaded portions of the drive wheel 143 and flexible piston rod 141 may be used to transmit force from the drive wheel to the piston rod 141. Accordingly, in the embodiment of FIG. 2, the drive wheel 143 is the driver while the flexible piston rod 141 is the driven member. The rotation of the drive wheel 143 can drive the flexible piston rod 141 forward in a linear longitudinal direction to cause the plunger engagement device 144 to nudge the plunger 125 within the fluid cartridge 120 so as to dispense fluid 126 therefrom.

Still referring to FIG. 2, the controller device 200 can include a user interface 222 that permits a user to monitor and control the operation of the pump device 100. In some embodiments, the user interface 222 can include a display device 223 and one or more user-selectable buttons (e.g., several buttons 224 including buttons 224a and 224b are shown in the embodiment of FIG. 2). Additionally or alternatively, the user interface 222 can include a touch-screen display device. The display device 223 can include an active area in which numerals, text, symbols, images, or a combination thereof can be displayed. For example, the display device 223 can be used to communicate a number of settings or menu options for the infusion pump assembly 20. In this embodiment, the user may press one or more of the buttons 224 to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224 of the user interface 222. For example, in embodiments of the infusion pump assembly 20 configured to dispense insulin, the user may press one or more of the buttons 224 to change the dispensation rate of insulin or to request that a bolus of insulin be dispensed immediately or at a scheduled, later time. In some implementations, the display device 223 may also be used to communicate information regarding remaining battery life. Further, in this embodiment, the user can accept or decline a suggested dosage of medicine by pressing either of buttons 224a and 224b of the user interface 222.

The controller device 200 can also be equipped with an inspection light device 228. The inspection light device 228 can provide the user with a tool to illuminate and inspect a targeted location. For example, the inspection light device 228 can be directed at the infusion site on the user's skin to verify that the infusion set is properly embedded, or the inspection light device 228 can be directed at the pump device 100 to illuminate the cavity 116 or other areas. The inspection light device 228 can also be used to notify the user to an alert condition of the pump assembly 20. An activation of the inspection light device 228 can thereby provide a visual notification (as an alternative to, or in addition to, the visual notification provided on the display device 223) to the user that attention to the infusion pump assembly 20 is warranted.

The controller device 200 of the pump assembly 20 also includes a wireless communication device 221, an NFC circuit 230, and an accelerometer 231. Each of these components can be in electrical communication with the control circuitry of the controller device 200. The wireless communication device 221 can facilitate wireless communications between the pump assembly 20 and the mobile device 40. As noted above, the wireless communication device 221 can send and receive data signals to and from the corresponding wireless communication device 41 of the mobile device 40 via a short-range wireless connection (e.g., RF, Wi-Fi, or Bluetooth connectivity). For example, the controller device 200 can receive a trigger signal to initiate a bolus dosage of insulin from the mobile device 40 via the communication devices 221 and 41.

In some embodiments, wireless communications between the controller device 200 and the mobile device 40 can incorporate one or more security measures to inhibit signal hijacking. As one example, a secure communications protocol involving security-coded wireless data packets can be implemented in wireless communications between the controller device 200 and the mobile device 40. As another example, the controller device 200 and the mobile device 40 can execute a wireless pairing routine to establish a one-to-one wireless connection. In some embodiments, the pairing may involve an exchange of unique information relating to the user (e.g., a passcode established by the user) of the devices.

In some embodiments, the trigger signal can include a suggested dosage amount. The suggested dosage amount can be determines by a dosage calculator application 44 executed by a controller 43 of the mobile device 40. In some embodiments, the dosage calculator application 44 determines the suggested dosage amount based on data indicative of a user's blood glucose level received from the glucose monitoring device 50a or the blood glucose test strip reader 50b. In some embodiments, the dosage calculator application 44 also utilizes data indicative of the rate of change in the user's blood glucose level and/or data indicative of the user's food consumption in determining the suggested medicine dosage amount.

In this example, the dosage calculator application 44 determines a suggested bolus dosage of insulin of 4.0 units. The suggested bolus dosage is presented to the user via the touchscreen 47 of the user interface 42. The user can accept or decline the suggested bolus dosage by interacting with the user interface 42 (e.g., by selecting the "YES" or "NO" option on the touchscreen 47). If the user accepts the suggested bolus dosage, the wireless communication device 41 can transmit a trigger signal to initiate the suggested bolus dosage to the controller device 200 of the pump assembly 20. The wireless communication device 221 of the controller device 200 can receive the trigger signal. The controller device 200 can provide a notification to the user indicating that a suggested bolus dosage has been received. The notification can be visual, audible, tactile, and a combination thereof. For instance, as depicted in this embodiment, the controller device can present the suggested bolus dosage to the user via the display device 223.

In some embodiments, the controller device 200 is configured to wait for confirmation at the pump assembly 20 that the suggested bolus dosage is acceptable to the user before initiating dispensation. As discussed below with reference to FIGS. 4A-C, user confirmation at the pump assembly 20 of an accepted bolus dosage may be provided in a variety of ways. If the user confirms acceptance of the bolus dosage via the user interface 222, the controller device 200 can cause the pump device to initiate dispensation of the suggested bolus dosage. In some embodiments, the controller device 200 may transmit a confirmation signal to the mobile device 40 to indicate that the suggested bolus dosage has been initiated. In some embodiments, if the user declines or chooses to modify the suggested bolus dosage, the controller device 200 may transmit a signal to the mobile device 40 to indicate the rejection or modification.

Referring to FIGS. 4A-C, in some embodiments, the infusion pump assembly 20 is pocket-sized so that the pump device 100 and controller device 200 can be worn in the user's pocket 6 or in another portion of the user's clothing. For example, the pump device 100 and the controller device 200 can be attached together and form the pump assembly 20 that comfortably fits into a user's pocket 6. The user can carry the portable infusion pump assembly 20 and use the tube 72 of the infusion set 70 to direct the dispensed medicine to the desired infusion site. In some circumstances, the user may desire to wear the pump assembly 20 in a more discrete manner. Accordingly, the user may pass the tube 72 from the pocket 6, under the user's clothing, and to the infusion site where the adhesive patch 78 is positioned. As such, the pump system 10 can be used to deliver medicine to the tissues or vasculature of the user in a portable, concealable, and discrete manner. Furthermore, the monitoring device 50a can be worn on the user's skin while the pump assembly 20 is carried by the user (e.g., in a pocket). As such, the monitoring device 50a can communicate information indicative of the user's blood glucose level to the pump assembly 20 via a wireless connection while the pump assembly 20 is used to deliver medicine through the infusion set 70. In this embodiment, the monitoring device 50a may be arranged on the user's skin at a location that is spaced apart from the infusion set 70.

FIG. 4A depicts a first user confirmation technique, where the user interfaces directly with the pump assembly 20. In this example, the user can respond to an alert (e.g., an audible chime or a vibration) from the pump assembly 20 indicating that a suggested bolus dosage has been received by removing the pump assembly 20 (at least the controller device 200 if detachable) from his/her pocket 6 and engaging the user interface 222 of the controller device 200. In some embodiments, the user can confirm acceptance, decline acceptance, or request a modification of the suggested bolus dosage via the user-selectable buttons 224 of the controller device 200. In response to receiving the confirmation of acceptance, the pump assembly 20 can initiate dispensation of the suggested bolus dosage.

FIG. 4B depicts a second user confirmation technique, where the user interfaces directly with the mobile device 40. In this example, the user can respond to the alert from the pump assembly 20 by engaging the user interface 42 of the mobile device 40. In some embodiments, the user can confirm acceptance, decline acceptance, or request a modification of the suggested bolus dosage via the user interface 42 (e.g., by selecting an appropriate option presented on the touch screen 47). In some embodiments, the user may be prompted to enter a security code to confirm acceptance of the suggested bolus dosage. In some embodiments, the user may be prompted to provide a biometric confirmation of acceptance, e.g., a fingerprint or facial recognition, via the user interface 42. In response to receiving the confirmation of acceptance, the mobile device 40 can transmit a confirmation signal to the pump assembly 20 to initiate dispensation of the suggested bolus dosage.

FIG. 4C depicts a third user confirmation technique, where the user can provide confirmation of an accepted suggested bolus dosage (wirelessly communicated from the mobile device 40 to the pump assembly 20) without directly viewing the pump assembly 20. In this embodiment, the user can respond to the alert from the pump assembly 20 by physically bumping the mobile device 40 against the pump assembly 20 (optionally, with one or more layers of clothing therebetween) while the pump assembly 20 remains in the user's pocket 6. As described below in connection with FIG. 6B, the pump assembly 20 can detect the bump and initiate dispensation of the suggested bolus dosage.

In some embodiments, the pump assembly 20 can detect a bump with the mobile device 40 via the NFC circuit 230 and/or the accelerometer 231. As one example, the bump from the mobile device 40 against the pump assembly (e.g., directly or indirectly such that both devices undergo a detectable bump impact) can cause a simultaneous data exchange between the NFC circuit 230 integrated in the controller device of the pump assembly 20 and the NFC circuit 46 in the mobile device 40. The data exchange may provide a confirmation signal to the pump assembly 20 indicating that the user has confirmed acceptance of the suggested bolus dosage. In some embodiments, the accelerometers 231 (in the pump assembly 20) and 45 (in the mobile device 40) can operate in conjunction with the NFC circuit 230 to supplement the criteria for activating communications between the NFC circuits 230 and 46. In other words, while in some embodiments, NFC communications are initiated based merely on proximity between the NFC circuits 230 and 46, in other embodiments a threshold movement of the pump assembly 20 and/or the mobile device 40 must be detected to activate NFC communication. An objective for including this feature can be to more clearly ascertain that the user desires to accept the suggested bolus dosage via NFC when the NFC circuits 230 and 46 are in range of one another. That is, by requiring the user to physically bump the mobile device 40 against the pump assembly 20, the user's intentions for accepting the suggested bolus dosage can be confirmed with a greater level of confidence.

In some embodiments, this optional feature of using the accelerometer 231 in conjunction with the NFC circuit 230 can function as follows. When a movement is detected by accelerometer 231, the characteristics of the movement can be compared by to a predetermined threshold value (e.g., a threshold movement indicative of the aforementioned "bump" or tap movement). If the detected movement is greater than or equal to the threshold value, the NFC circuit 230 can potentially be activated. But, if no movement that is greater than or equal to the threshold value is detected, the NFC circuit 230 is not activated (even if the NFC circuit 230 is within the required proximity of the NFC circuit 46 such that NFC communications can potentially be performed). Therefore, in some embodiments this feature operates to enable NFC when the following two conditions are simultaneously met, or are both met within an establish time interval: (i) an acceleration or an acceleration profile that is greater than or equal to a threshold value is detected (indicating, e.g., a tap or other "bump" action between the pump assembly 20 and the mobile device 40), and (ii) the NFC circuit 230 is in proximity with the NFC circuit 465 such that communications therebetween using NFC can occur. In some embodiments, the accelerometer 45 can be similarly operated in conjunction with the NFC circuit 46 of the mobile device 40.

In some embodiments, the accelerometers 231 and 45 can be used to detect a bump independently of the NFC circuits 230 and 46. For example, the pump assembly 20 can detect the bump by sensing a movement via the accelerometer 231 and receiving bump confirmation signal from the mobile device 40 via the wireless communication devices 221 and 41. In some embodiments, the bump confirmation signal must be received within a predetermined time window (e.g., about 0.5 seconds to about 2 seconds) to be considered a detectable bump by the pump assembly 20. In some embodiments, the pump assembly 20 is configured to delay dispensation until a pattern of bumps (e.g., two or more bumps) is detected. This feature may reduce the likelihood of inadvertent acceptance of the suggested bolus dosage by a false-positive bump. In some embodiments, the NFC circuits 230 and 46 can communicate a unique identifier (e.g., a serial number) to one another as a security code to establish a one-to-one NFC connection. This feature may reduce the likelihood of an inadvertent acceptance of the suggested bolus dosage, for example, if the user accidently bumps his/her infusion pump assembly into another user's mobile device.

In some embodiments, as similar bump technique for NFC as described above for user-confirmation of an accepted bolus dosage can be used to send the original trigger signal (described above as being implemented by short range wireless communication). For example, a suggested dosage determined by the dosage calculator application 44 could be coded into the NFC circuit 46 of the mobile device 40 and transmitted by an NFC-bump to the NFC circuit 230 (and therefore the control circuitry) of the pump assembly 20.

Figure 5:
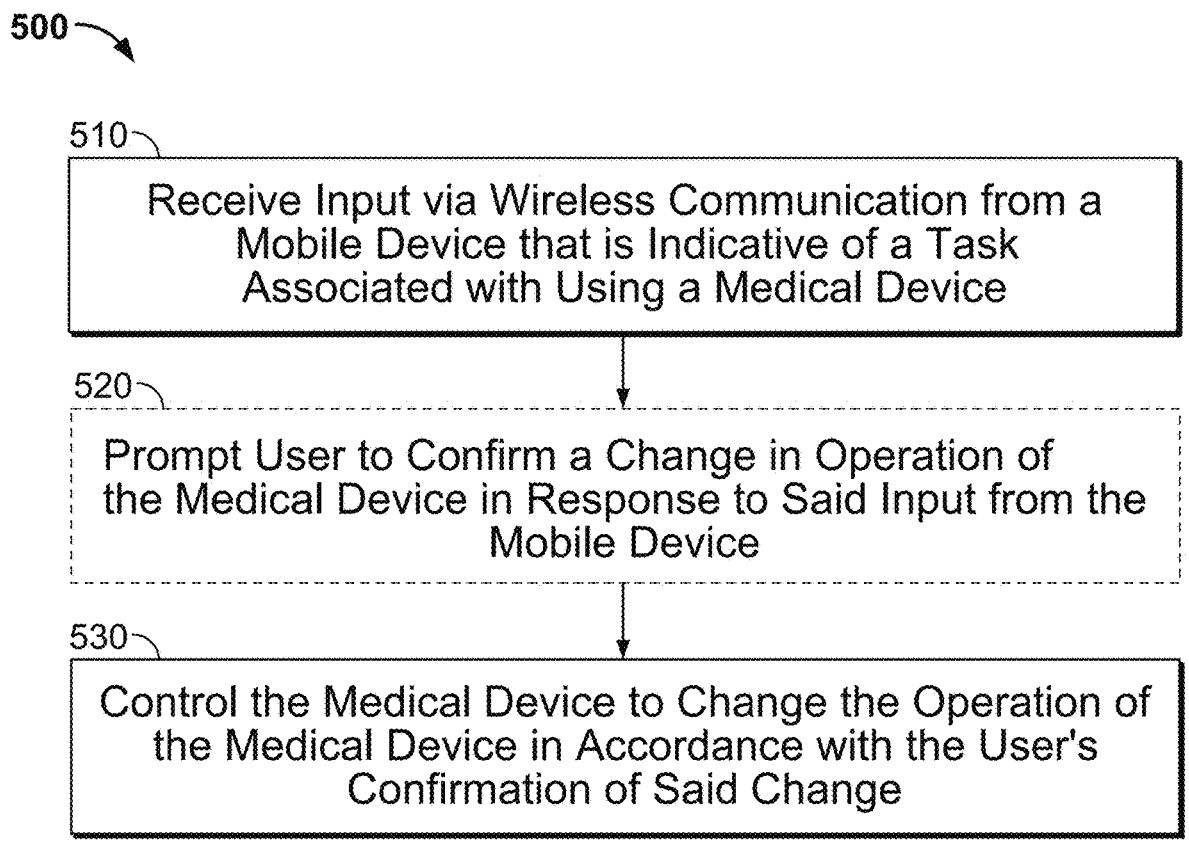
FIG. 5 is a flowchart of an example process for operating a medical device with wireless communication capabilities in accordance with some embodiments.

Referring now to FIG. 5, the control circuitry of a medical device (e.g., an infusion pump assembly) that includes wireless communication equipment can implement a process 500 of receiving commands from a mobile device, and controlling the medical device in accordance with received commands. Such a process 500, for example, can be implemented by the control circuitry housed in the controller device 200 of an infusion pump assembly 20 (FIGS. 2-3). However, this document is not necessarily limited to any particular medical device with respect to process 500.

In operation 510, the control circuitry of a medical device can receive input via wireless communication from a mobile device (e.g., a smartphone). The input can be indicative of a task associated with using the medical device. A medical device that can perform operation 510 is exemplified in FIGS. 2-3, where a wireless communication device 221 and an NFC circuit 230 are in electrical communication with the control circuitry of a controller device 200 of an infusion pump assembly 20. As explained above, the wireless communication device 221 and the NFC circuit 230 of the pump assembly 20 can function to receive and send communications from a corresponding wireless communication device 41 and NFC circuit 46 of the mobile device 40. An example of operation 310 is provided in FIGS. 2-3, where dosage calculator application 44 of the mobile device 40 determines a suggested bolus dosage of insulin (or another medication) and transmits a trigger signal to the pump assembly 20 via the wireless communication devices 41 and 221.

In operation 520, the control circuitry optionally provides a prompt for the user to confirm a change in the operation of the medical device in response to input received from the mobile device. Such a prompt may be advantageously used to confirm the user's intent to change the operation of the medical device before the control circuitry actually implements the change. An example of operation 520 is provided in FIGS. 2-3, where the control circuitry of the controller device 200 of the pump assembly 20 generated the illustrated textual prompt on the display 223. The prompt provides a description of the potential change in operation ("Bolus Initiated from Mobile Device; Deliver Requested Bolus? 4.00 Units"). Alternatively or additionally, other techniques can be used for prompting the user to confirm the user's intent to change the operation of the medical device. For example, the medical device can provide a visual (e.g., a flashing light), auditory (e.g., a chime) and/or tactile (e.g., vibration) alert. As described above, by pressing a button 224a of the user interface 222, the user can confirm the user's intent to implement a change in the operation of the infusion pump assembly 20. As described in connection with FIGS. 4A-C, the user can provide confirmation by interacting directly with the pump assembly 20 and/or the mobile device 40 via a user interface, or by bumping the mobile device against the pump assembly 20. In some embodiments, the user confirmation techniques of FIGS. 4A-C can be modified or combined to achieve an acceptable level of security and reliability.

In operation 530, after receiving confirmation from the user to implement the change associated with the input from the mobile device, the control circuitry can control the medical device to change the operation of the medical device in accordance with the user's confirmation of the change. Again in regard to the example of FIGS. 2-3, when the user confirms the change to the infusion pump assembly 20 related to the suggested bolus dosage, the control circuitry of the controller device 200 can thereafter control the pump device 100 to deliver the corresponding bolus dispensation of insulin.

Figure 6:
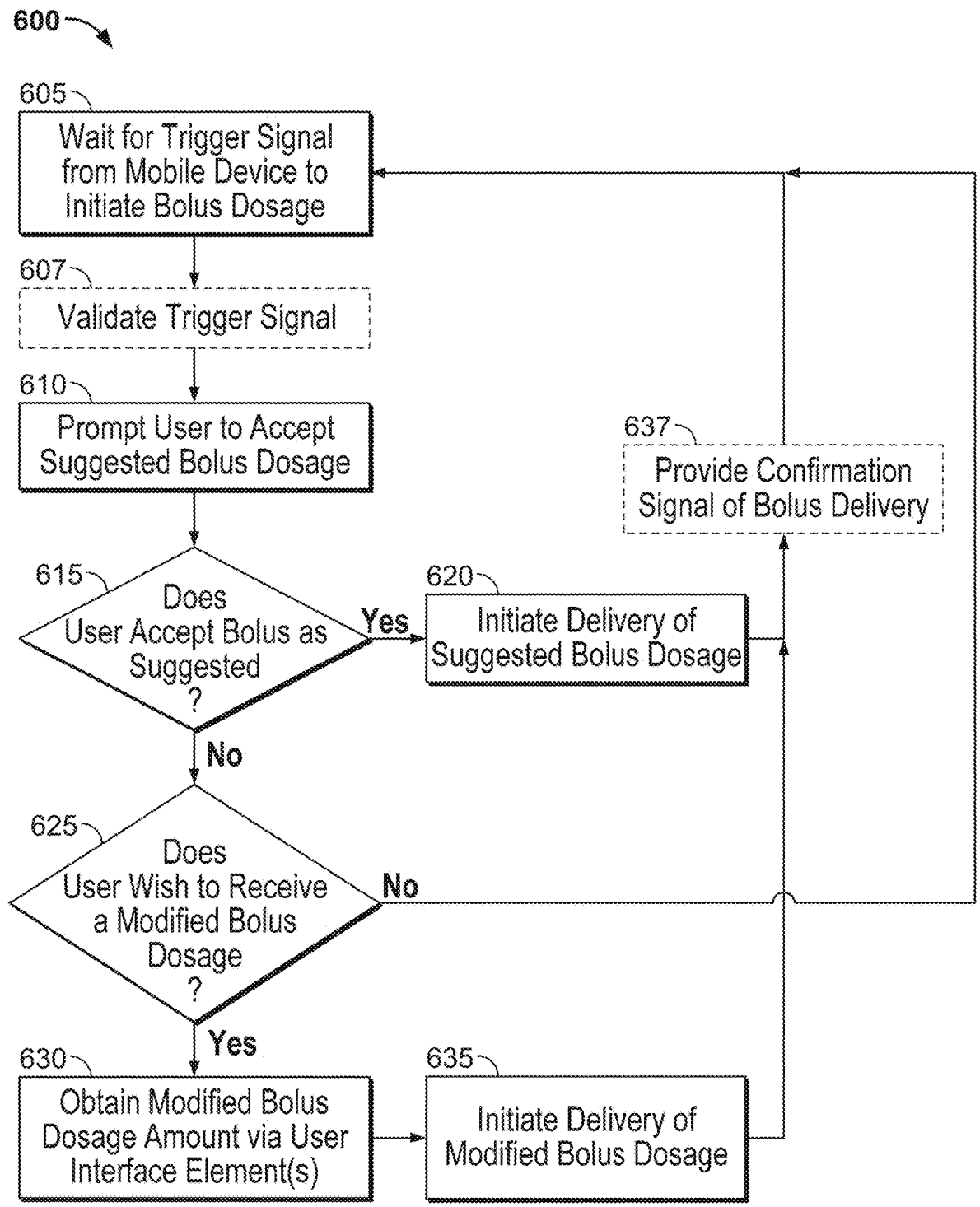
FIG. 6 is a flowchart of an example process for using an infusion pump assembly equipped with wireless communication capabilities in accordance with some embodiments.

Referring now to FIG. 6, the infusion pump assembly 20 can dispense a bolus dosage of medicine suggested by the mobile device 40 after receiving confirmation that the suggested bolus dosage is accepted by the user. For example, a process 600 for dispensing a suggested bolus dosage can be implemented by the controller device 200 of the pump assembly 20. In operation 605, the controller device 200 can wait for a trigger signal from the mobile device 40 to initiate a bolus dosage (e.g., a bolus dosage determined by the dosage calculator application 44). The trigger signal may be received via short-range wireless communication or NFC. In operation 607, the controller device 200 can optionally validate the trigger signal. In some embodiments, validating the trigger signal may include detecting a signal strength of the short-range wireless connection between the pump assembly 20 and the mobile device 40, and comparing the signal strength to a predetermined threshold. The controller device 200 may only validate a trigger signal if the detected signal strength is greater than the threshold. An objective for this feature can be to verify that the mobile device 40 is close in proximity to the pump assembly 20, which increases the reliability that the trigger signal originated from a mobile device in the user's possession. In some embodiments, validating the trigger signal may include applying a unique decryption key to trigger signal that has been encrypted.

In operation 610, the user is prompted to accept the suggested bolus dosage indicated by the trigger signal. At operation 615, the controller device 200 determines if the user accepts the suggested bolus dosage. In operation 620, if the user accepts the suggested bolus dosage (615), the controller device 200 initiates delivery of the suggested bolus dosage via the pump device 100. If the user declines the suggested bolus dosage (615), the controller device 200 can prompt the user for a modified bolus dosage (e.g., via a prompt script provided on the display device 223). In operation 625, the controller device determines if the user wishes to receive a modified bolus dosage. In operation 630, if the user wishes to receive a modified bolus dosage (625), the controller device 200 can obtain the modified bolus dosage amount via the user interface elements (e.g., the user-selectable buttons 224). And in operation 635, the controller device 200 can initiate delivery of the modified bolus dosage via the pump device 100. At operation 637, the controller device 200 can optionally provide a confirmation signal indicative of an initiated bolus delivery. For example, the controller device 200 can provide a visual, auditory, or tactile alert perceptible by the user and/or transmit a confirmation signal to the mobile device 40. After a suggested (620) or modified (635) bolus dosage is initiated, or after the suggested (615) and modified (625) dosages have been declined by the user, the process 600 can return to operation 605, where the controller device 200 can wait for a subsequent trigger signal to initiate another bolus dosage.

Figure 6A:
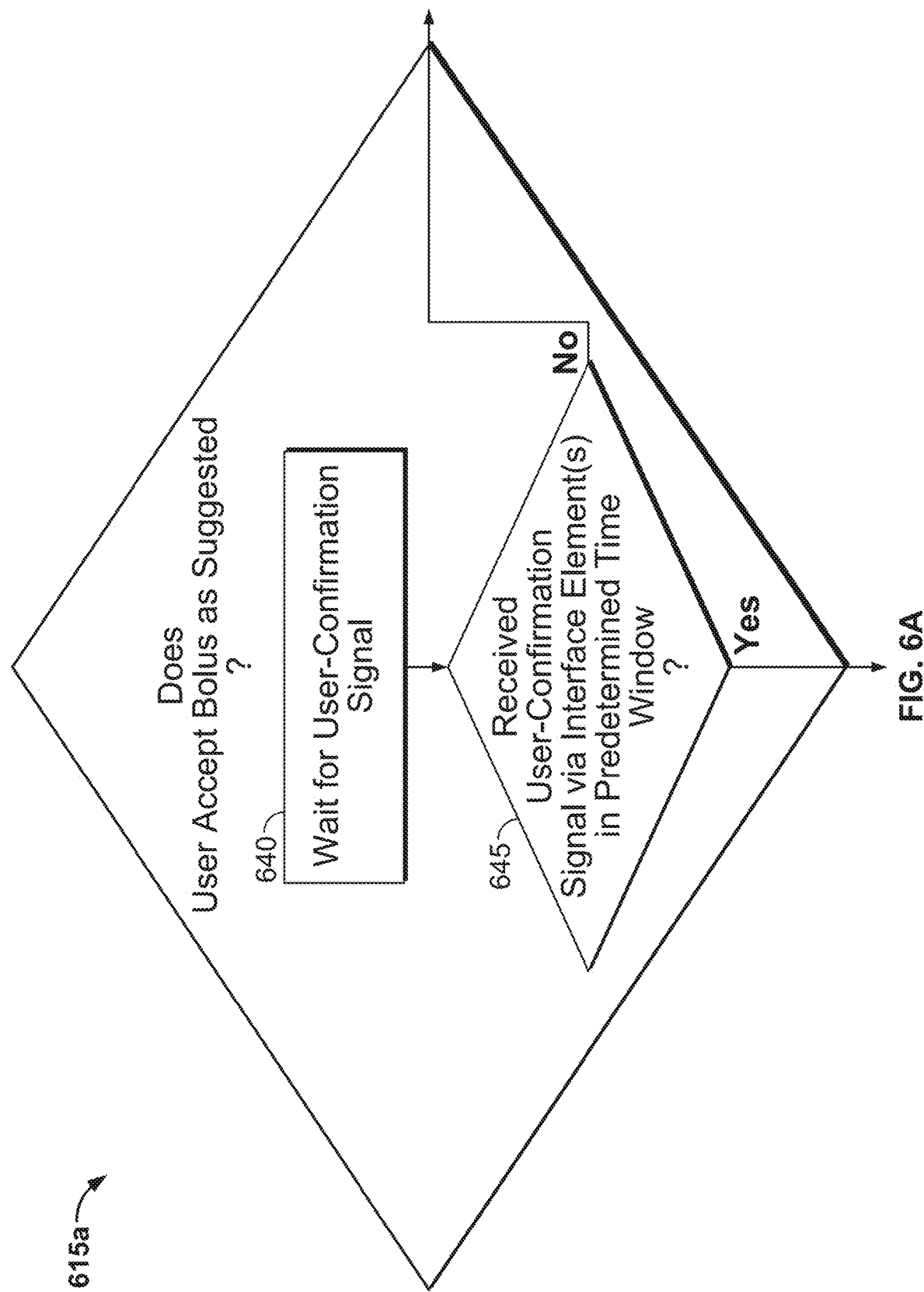
FIG. 6A is a flowchart of a first example process for determining whether a user as accepted a suggested bolus dosage.
Figure 6B:
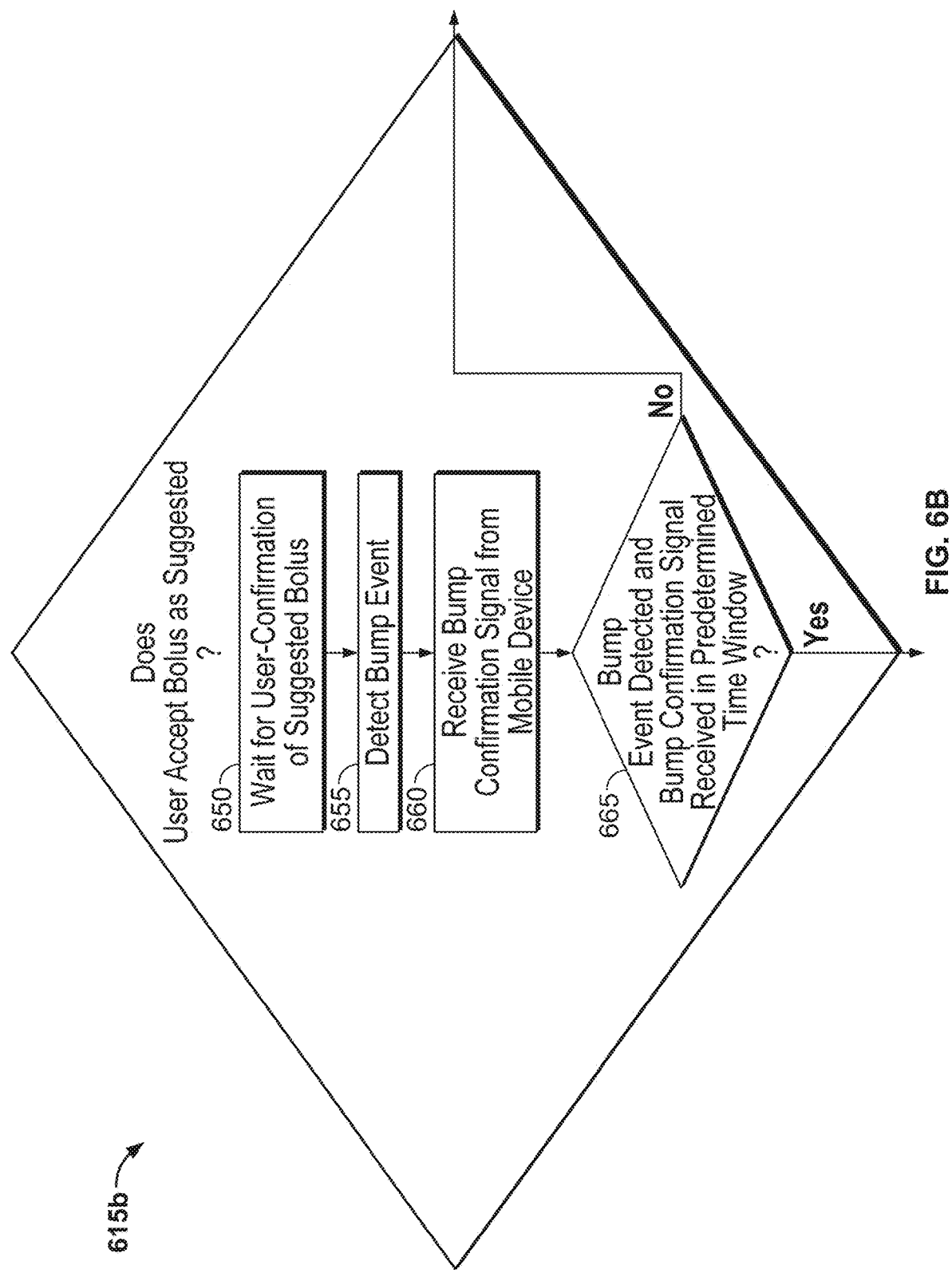
FIG. 6B is a flowchart of a second example process for determining whether a user as accepted a suggested bolus dosage.

Revisiting operation 615, FIG. 6A depicts a first example sub-process 615a executable by the controller device 200 for determining whether the user accepts the suggested bolus dosage. In operation 640, the controller device 200 can wait for a user-confirmation signal indicating that the user has accepted the suggested bolus dosage. In operation 645, the controller device can determine whether a user-confirmation signal has been received via one or more user interface elements (e.g., the user selectable buttons 624) of the user interface 222 within a predetermined time window (e.g., between about 0.5 seconds and about 15 seconds). If the user-confirmation signal is not received within the time window (645), the controller device 200 can determine that the user does not accept the suggested bolus dosage. If the user-confirmation signal is received within the time window (645), the controller device 200 can determine that the user does accept the suggested bolus dosage. An example of the sub-process 615a is provided in FIGS. 2-3 and 4A, where the user-confirmation signal is received when the user selects the button 224a corresponding to the "Accept" option presented on the display device 223. If the user selects the button 224a within the predetermined time window, the controller device 200 can determine that the user accepts the suggested bolus dosage. However, if the user does not select the button 224a within the predetermined time window, or if the user selects the button 224b corresponding to the "Decline" option, the controller device 200 can determine that the user does not accept the suggested bolus dosage. In some embodiments, if the sub-process 615a times out (e.g., if the user confirmation signal is not received in the predetermined time window), the controller device 200 may provide a reminder alert to the user.

FIG. 6B depicts a second example sub-process 615b executable by the controller device 200 for determining whether the user accepts the suggested bolus dosage. In operation 650, the controller device 200 can wait for a user confirmation of the suggested bolus. In operation 655 the controller device 200 can detect a bump event. In operation 660, the controller device 200 can receive a bump-confirmation signal from the mobile device 40. In operation 665, the controller device 200 can determine whether the bump-event confirmation signal was received within a predetermined time window (e.g., about 0.5 seconds to about 2 seconds) starting from the bump event detection. If the bump-confirmation signal is not received within the time window (665), the controller device 200 can determine that the user does not accept the suggested bolus dosage. If the bump-confirmation signal is received within the time window (665), the controller device 200 can determine that the user does accept the suggested bolus dosage.

An example of the sub-process is provided FIG. 4C, where the controller device 200 is described as operable to detect a bump event using NFC communication via an NFC circuit 230 of the controller device 200. As yet another example described in connection with FIG. 4C, an accelerometer 231 integrated with the control circuitry of the controller device 200 can detect movement indicative of a bump event. If the mobile device 40 independently detects the bump event via its NFC circuit 46 and/or accelerometer 45 it can transmit a bump-confirmation signal the controller device 200. In some embodiments, e.g., when the bump event is detected via NFC communication, the bump-confirmation signal may be received simultaneously with the bump event detection via two-way communication between the NFC circuits 230 and 46.

Figure 6C:
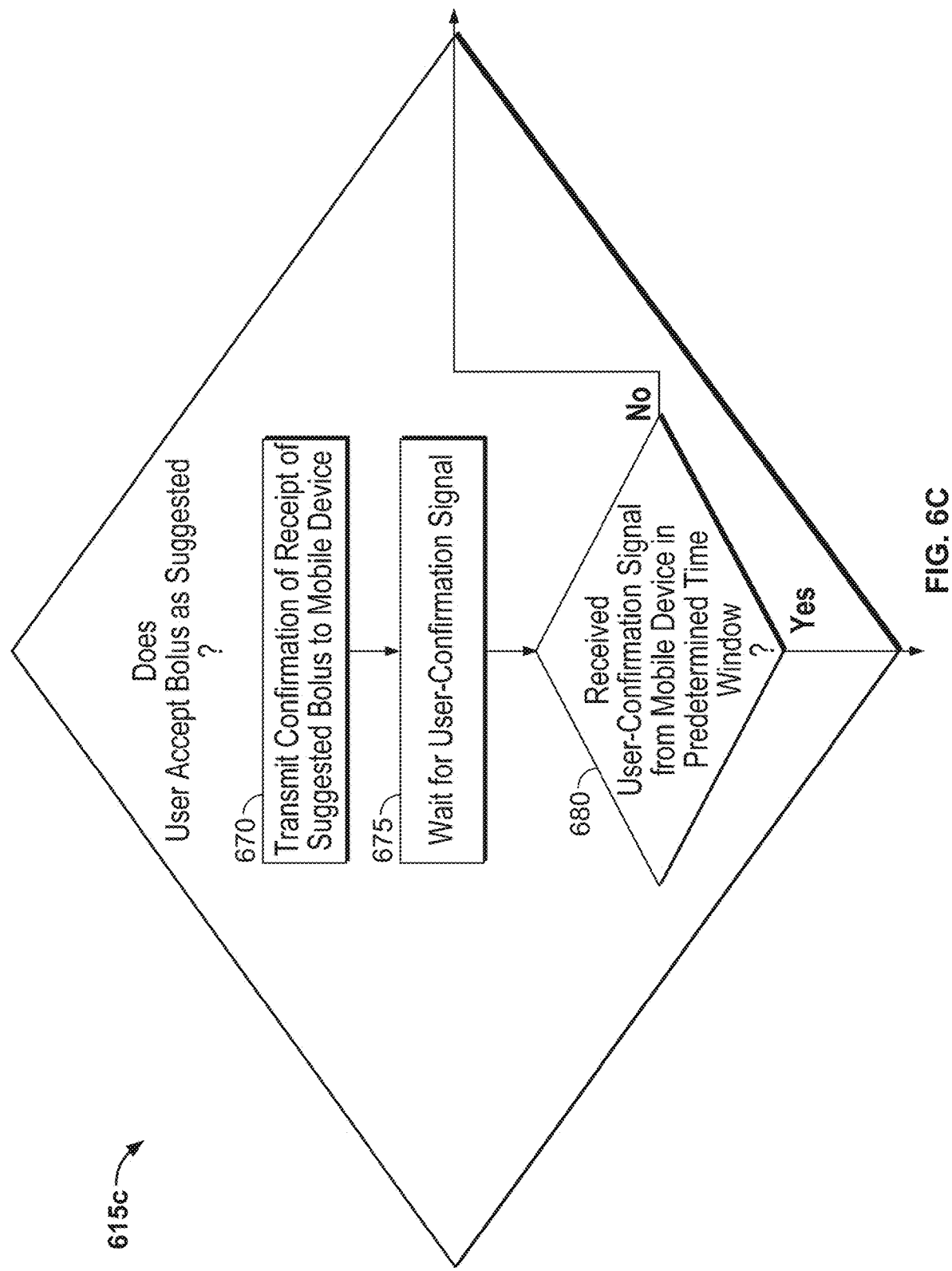
FIG. 6C is a flowchart of a third example process for determining whether a user as accepted a suggested bolus dosage.

FIG. 6C depicts a third example sub-process 615c executable by the controller device 200 for determining whether the user accepts the suggested bolus dosage. In operation 670, the controller device can transmit (e.g., via short-wireless connection or NFC connection) a confirmation signal to the mobile device 40 indicating receipt of the suggested bolus dosage via the trigger signal. In operation 675, the controller device 200 can wait for a user-confirmation signal indicating that the user has accepted the suggested bolus dosage. In operation 680, the controller device 200 can determine whether a user-confirmation signal has been received from the mobile device 40 within a predetermined time window (e.g., between about 0.5 seconds and about 15 seconds). If the user-confirmation signal is not received within the time window (680), the controller device 200 can determine that the user does not accept the suggested bolus dosage. If the user-confirmation signal is received within the time window (680), the controller device 200 can determine that the user does accept the suggested bolus dosage. An example of the sub-process 615a is provided in FIG. 4B, where the user engages the user interface 42 of the mobile device 40 to confirm acceptance, decline acceptance, or request a modification of the suggested bolus dosage. For example, in some embodiments, the user may be prompted to provide a security code to confirm acceptance or a biometric confirmation of acceptance, e.g., a fingerprint or facial recognition, via the user interface 42. If the user confirms acceptance via the user interface 42 within the predetermined time window, the controller device 200 can determine that the user accepts the suggested bolus dosage. However, if the user does not confirm acceptance using the user interface 42 within the predetermined time window, or if the user declines the suggested bolus dosage (or request a modified dosage) using the user interface 42, the controller device 200 can determine that the user does not accept the suggested bolus dosage.

Figure 7:
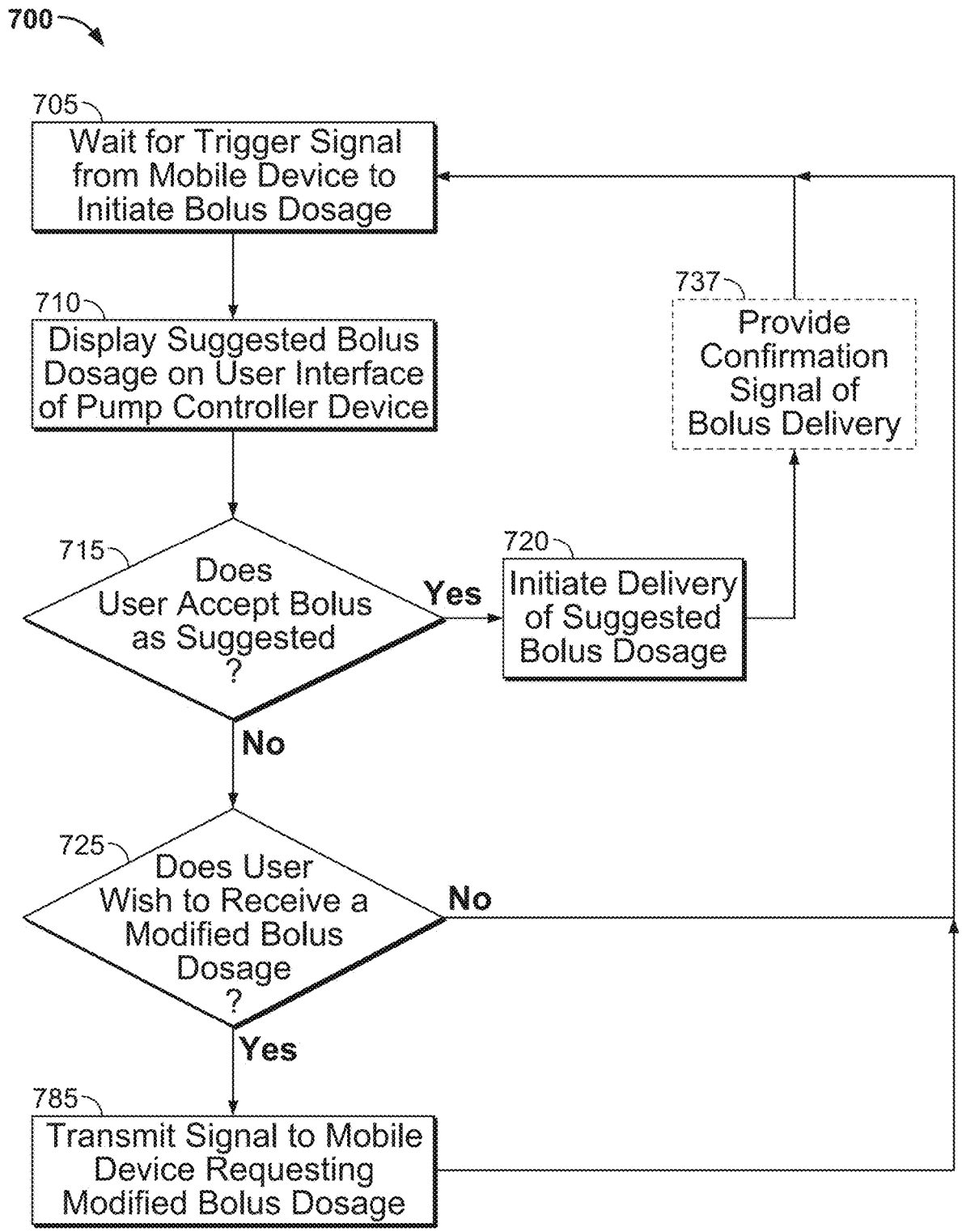
FIG. 7 is a flowchart of an alternative example process for using an infusion pump assembly equipped with wireless communication capabilities in accordance with some embodiments.

Referring now to FIG. 7, an alternative process 700 for dispensing a suggested bolus dosage can be implemented by the controller device 200 of the pump assembly 20. Operations 705-725 are similar to operations of the process 600. In operation 705, the controller device 200 can wait for a trigger signal from the mobile device 40 to initiate a bolus dosage (e.g., a bolus dosage determined by the dosage calculator application 44). The trigger signal may be received via short-range wireless communication or NFC. In operation 710, the user is prompted to accept the suggested bolus dosage indicated by the trigger signal. In operation 720, if the user accepts the suggested bolus dosage (715), the controller device 200 initiates delivery of the suggested bolus dosage via the pump device 100. At operation 715, the controller device determines if the user accepts the suggested bolus. If the user declines the suggested bolus dosage (715), the controller device can prompt the user for a modified bolus dosage. At operation 737, the controller device 200 can optionally provide a confirmation signal indicative of an initiated bolus delivery. For example, the controller device 200 can provide a visual, auditory, or tactile alert perceptible by the user and/or transmit a confirmation signal to the mobile device 40.

At operation 725, the controller device determines if the user wishes to receive a modified bolus dosage. At operation 785, if the user wishes to receive a modified bolus dosage (725), the controller device 200 can transmit a signal to the mobile device 40 requesting a modified bolus dosage. In some embodiments, the mobile device 40 can prompt the user, e.g., via the user interface 42, to provide a modified dosage or to provide new data for the dosage calculator application 44 to consider in determining a suggested bolus dosage. After a suggested bolus dosage is initiated (720) or declined (725), or after a modified dosage has been requested (785), the process can return to operation 705, where the controller device 200 can wait for a subsequent trigger signal to initiate another bolus dosage.

Figure 8:
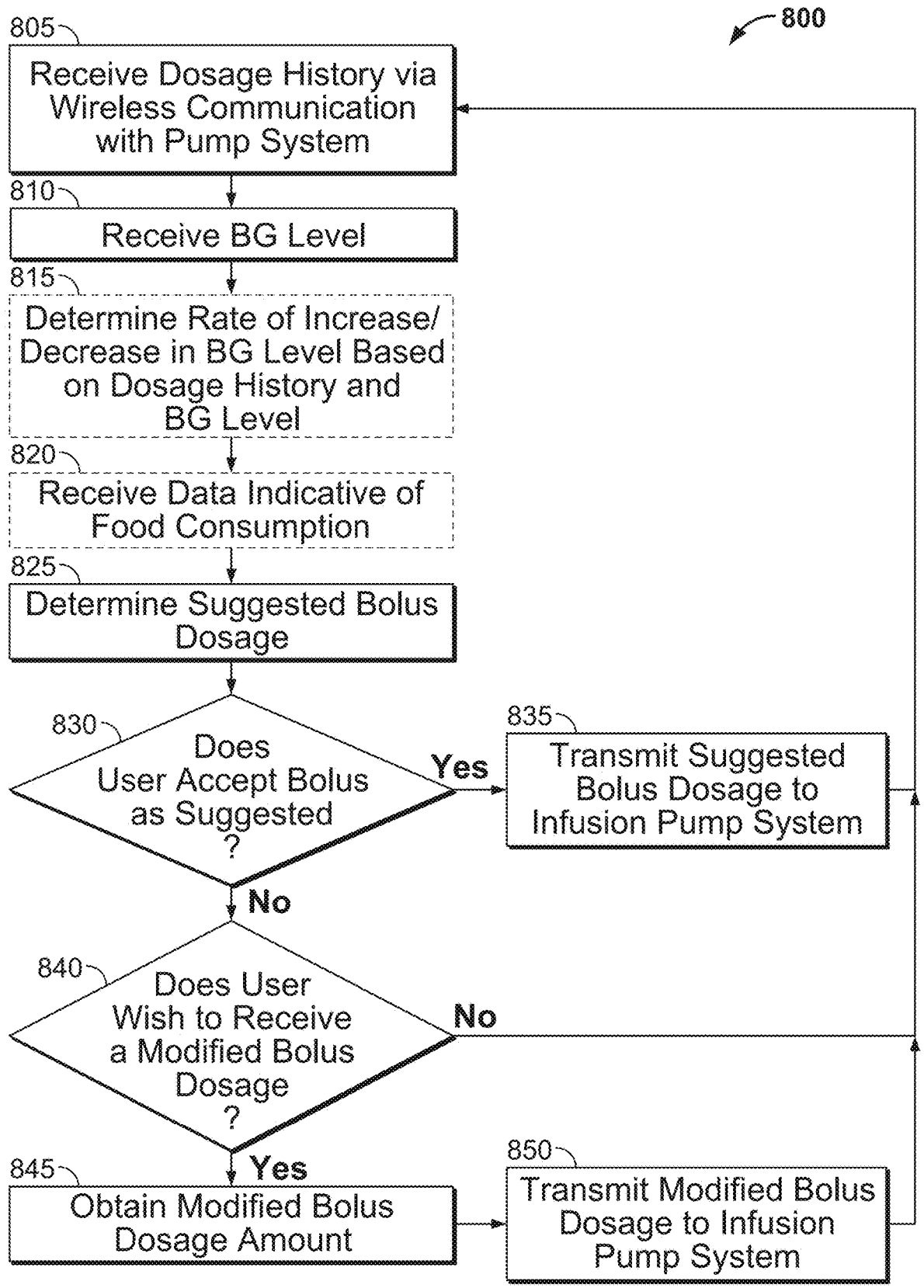
FIG. 8 is a flow chart of an example process for using a mobile device equipped with wireless communications capabilities in accordance with some embodiments.

Referring now to FIG. 8, the dosage calculator application 44 executed by the controller 43 of the mobile device 40 can determine a suggested bolus dosage based on data indicative of the user's blood glucose level. For example, a process 800 for determining a suggested bolus dosage and providing the suggested dosage to an infusion pump assembly 20 can be implemented by the mobile device 40. As previously described, the pump assembly 20 can operate to deliver insulin to the user by basal dosages, selected bolus dosages, or a combination thereof. A basal rate of insulin can be delivered in an incremental manner (e.g., dispense 0.25 U every fifteen minutes for a rate of 1.0 U per hour) to help maintain the user's blood glucose level within a targeted range during normal activity, when the user is not consuming food items. The user may select one or more bolus deliveries, for example, to offset the blood glucose effects caused by food intake, to correct for an undesirably high blood glucose level, to correct for a rapidly increasing blood glucose level, or the like. In some circumstances, the basal rate pattern may be programmed by a health care professional during a clinical visit (or, optionally, by the user) and may remain at a substantially constant rate for a long period of time (e.g., a first basal dispensation rate for a period of hours in the morning, and a second basal dispensation rate for a period of hours in the afternoon and evening). In contrast, the bolus dosages can be dispensed in user-selected amounts based on calculations made by the dosage calculator application 44. For example, the dosage calculator application 44 can determine that the user's blood glucose level is rapidly increasing (e.g., by interpreting data received from the glucose monitoring device 50a and/or the blood glucose test strip reader 50b, or the like) and can make a suggestion to the user to administer a bolus of insulin to correct for the rapid increase in blood glucose level. In another example, the user can request (via the user interface 42) that the dosage calculator application 44 calculate and suggest a bolus dosage based, at least in part, on a proposed meal that the user plans to consume.

The basal and bolus insulin dispensed into the user's system may act over a period of time to control the user's blood glucose level. As such, the user can benefit from the embodiments of the infusion pump system 10 that can take into account different circumstances and information when determining the amount of a bolus dosage to suggest to the user. For example, the dosage calculator application 44 may be triggered to suggest a bolus dosage in response to the user's input of meal information (See FIGS. 2-3). When calculating the bolus dosage, however, the user may benefit if the dosage calculator application 44 employed information, in addition to the meal information, when calculating the bolus dosage. In some embodiments, the dosage calculator application 44 can use information such as data indicative of the user's blood glucose level, food intake data recently submitted by the user via the user interface 42 of the mobile device 40, the user's insulin load, and the like. Exemplary information that can be derived from the user's blood glucose information that can be used by the dosage calculator application 44 in determining a bolus dosage can include the user's current blood glucose level, the rate of change in the user's blood glucose level, the $2^{nd}$ derivative of the user's blood glucose data, the shape and/or appearance of the user's blood glucose curve, or the like. In some embodiments, the dosage calculator application 44 can use information from previously entered meals and previously delivered insulin dosages when calculating a suggested bolus dosage. In these embodiments, information regarding previously entered meals and previously delivered insulin dosages from 12 hours or more (e.g., 24 hours, 12 hours, 8 hours, 6 hours, 0.5 hours, or the like) can be used in the bolus dosage calculations.

In some embodiments, the controller device 200 may implement one or more operations of the process 800 (FIG. 8) to determine and suggest an insulin bolus dosage which includes a food offsetting component, a blood glucose correction component, and an insulin load correction component. The food offsetting component can represent an insulin bolus dosage to offset food intake data that have not previously been offset by an earlier bolus dosage. The blood glucose correction component can represent an insulin bolus dosage to maintain or return the user's blood glucose level to a targeted value within a predetermined range. This component can be derived from data indicative of a user's blood glucose level such as the user's current blood glucose level and the recent rate of change in the user's blood glucose level. The insulin load correction component can take into account insulin that has been previously received and food that has been previously consumed, but has not acted on the user. For example, the delay between a subcutaneous delivery of a bolus dosage of insulin and the peak plasma insulin level achieved from this bolus can be one hour or more. Additionally, the bolus dosage may not enter the subcutaneous tissue all at once. As such, the effect of the bolus can peak at about one to two hours and then decay in a predictable manner over as much as eight hours or. Due to the time decay effects of insulin activity, the user could be susceptible to request a subsequent bolus dosage while some insulin from a previously delivered bolus dosage has not yet acted upon the user (a scenario sometimes referred to as "bolus stacking"). To reduce the likelihood of undesirable bolus stacking, the insulin load information can be determined by dosage calculator application 44 on a periodic basis so that the user can be aware of the previously dispensed insulin which has not yet acted in the user's body. In a similar manner, food that has been previously consumed does not instantaneously act on the user and have its effects quickly decay. Depending on the type of food consumed, the effects of the food can be delayed and then slowly decay over time. In particular embodiments, the insulin load correction component may correct for the delayed effects of both previously delivered insulin and previously consumed food items.

Referring in more detail to FIG. 8, the illustrative process 800 for determining a suggested bolus dosage and providing the suggested dosage to an infusion pump assembly 20 can include a number of operations performed by various components of the mobile device 40. In operation 405, the dosage calculator application 44 can wait for a trigger to initiate a bolus dosage calculation. Exemplary triggers that can cause the dosage calculator application 44 to initiate a bolus dosage calculation can include a user input of food intake data (e.g., via the user interface 42 of the mobile device 40), an input of blood glucose data (e.g., as measured and transmitted wirelessly by the glucose monitoring device 50a and/or the blood glucose test strip reader 50b), a user request for a bolus dosage, the user's blood glucose level exceeding a predetermined threshold level, the user's blood glucose level increasing at a high rate greater than a predetermined threshold rate, or the like. In some embodiments, the suggested bolus dosage value can be calculated based on at least two of the three components as previously described: the food offsetting component, the blood glucose correction component, and the insulin load correction component. It should be understood from the description herein that the components can be contemporaneously calculated to provide the suggested bolus dosage value or, alternatively, calculated in discrete steps and then combined to provide the suggested bolus dosage value.

In operation 805, a dosage history is a received via wireless communication (e.g., NFC or short-range wireless communication) with the pump assembly 20. The dosage history may include data indicative of one or more previous bolus dosages initiated by the controller device 200 of the pump assembly 20. In some embodiments, data included in the dosage history can include a date/time data point and a quantity data point corresponding to each of the previous bolus dosages. In operation 810, the user's current blood glucose is received. As described above, the user's current blood glucose level can be received via wireless communication from the glucose monitoring device 50a and/or the blood glucose test strip reader 50b, or entered manually by the user via the user interface 42 of the mobile device 40. In operation 810, the dosage calculator application 44 can determine a rate of change (e.g., increase or decrease) based on the dosage history and the blood glucose level. Non-limiting examples of suitable techniques for determining the rate of change in the user's blood glucose level are described in U.S. application Ser. No. 12/348,162 filed on Jan. 2, 2009, the entirety of which is hereby incorporated by reference. Alternatively, the user may manually enter the rate-of-change information for his or her blood glucose level (rather than this information being determined by the dosage calculator application 44). For example, when using a blood glucose test strip reader 50b, the test strip reader may store blood glucose measurements performed by the user, which can be used to determine the rate of change in the user's blood glucose level. When prompted by the dosage calculator application 44, the user may enter the most recent rate of change data. In operation 820, the user can optionally enter data indicative of food intake (e.g., a meal that is about to be consumed, a meal that has recently been consumed, or the like). For example, if the user is testing his or her blood glucose level before consuming a meal, the user may input such food intake information when inputting the blood glucose level.

After the user's blood glucose information is obtained (e.g., via operations 805, 810, 815, and 820), in operation 825, the dosage calculator application 44 can determined a suggested bolus dosage based on the obtained data. As noted above, in some embodiments, the suggested bolus dosage value can be calculated by the dosage calculator application 44 based on at least two of the three components as previously described: the food offsetting component, the blood glucose correction component, and the insulin load correction component. Non-limiting examples of suitable techniques for determining a suggested bolus dosage are described in U.S. application Ser. No. 12/348,162 filed on Jan. 2, 2009, which (as described above) is incorporated herein by reference.

In operation 830, the dosage calculator application 44 can determine if the user accepts the suggested bolus dosage. For example, illustrated in FIGS. 2-3, the user can select the "YES" or "NO" option via the touchscreen user interface 42 of the mobile device 40 to accept or decline the suggested bolus dosage. In operation 835, if the accepts the suggested bolus dosage (830), the dosage calculator application 44 can cause the suggested bolus dosage to be transmitted to the infusion pump assembly 20 (e.g., in the form of a trigger signal via NFC or short-range wireless communication). If the user declines the suggested bolus dosage (840), the dosage calculator application 44 can prompt the user for a modified dosage. In operation 840, the dosage calculator application 44 can determine if the user wishes to receive a modified bolus dosage. In operation 845, if the user wishes to receive a modified bolus dosage (840), the dosage calculator application 44 can obtain the modified bolus dosage. For example, the user can enter a modified bolus dosage or provide additional data that can be used to calculate a modified dosage via the user interface 42. In operation 850, the dosage calculator application 44 can cause the modified bolus dosage to be transmitted to the pump assembly 20 (e.g., in the form of a trigger signal via NFC or short-range wireless communication). After a suggested (835) or modified (850) bolus dosage has been transmitted to the pump assembly, or after the user has declined the suggested and modified dosages (840), the process 800 can return to operation 802, where the dosage calculator application can wait for a subsequent trigger to initiate a bolus dosage calculation.

Various embodiments described herein include the mobile device 40 in the form of a smartphone device. The smartphone device 40 may store or otherwise execute the previously described dosage calculator application 44, and may further include other applications, computing sub-systems, and hardware. For example, a call handling unit may receive an indication of an incoming telephone call and provide a user the capability to answer the incoming telephone call. A media player may allow a user to listen to music or play movies that are stored in local memory of the smartphone device 40. The smartphone device 40 may include a digital camera sensor, and corresponding image and video capture and editing software. An internet browser may enable the user to view content from a web page by typing in an addresses corresponding to the web page or selecting a link to the web page.

Additionally, the smartphone device 40 may include an antenna to wirelessly communicate information with one or more base stations of a mobile telephone cellular network that enables the smartphone device 40 to maintain communication with a network as the smartphone device 40 is geographically moved. The smartphone device 40 may alternatively or additionally communicate with the network through a Wi-Fi router or a wired connection (e.g., ETHERNET, USB, or FIREWIRE).

Also, the smartphone device 40 can connect with an application store to provide a user of the smartphone device 40 the ability to browse a list of remotely stored application programs (such as the dosage calculator application 44 or other mobile applications) that the user may download over the network and install on the mobile computing device. The application store may serve as a repository of applications developed by third-party application developers. An application program (such as the dosage calculator application 44) that is installed on the smartphone device 40 may be able to communicate over the network with server systems that are designated for the application program. The smartphone device 40 may access cloud-based application programs, and the dosage calculator application 44 may be implemented as such as cloud-base application program. Cloud-computing provides application programs (e.g., a word processor or an email program) that are hosted remotely from the smartphone device 40, and may be accessed by the smartphone device 40 using a web browser or a dedicated program. In the embodiment described above, the smartphone device 40 stores the computer readable instructions so as to activate the dosage calculator application 44, which can be installed and run on the smartphone device 40 or can at least partially hosted at a server as part of a cloud-based application program. These and other services may be implemented in a server system. A server system may be a combination of hardware and software that provides a service or a set of services. For example, a set of physically separate and networked computerized devices may operate together as a logical server system unit to handle the operations necessary to offer a service to hundreds of computing devices.

A number of embodiments of the invention have been described. Nevertheless, it will be understood that various modifications may be made without departing from the spirit and scope of the invention. Accordingly, other embodiments are within the scope of the following claims.

What is claimed is:

1. A medical infusion pump system, comprising:
   a pump assembly that includes a pump device and a controller device, wherein the pump device is operable to receive a fluid cartridge and is in a first housing, the controller device is operable to control the pump device and is in a second housing, and the first housing and the second housing are configured to slidably engage one another; and
   a mobile device comprising a memory for storing computer-readable instructions to access a dosage calculator application for calculating a suggested medication bolus dosage, the mobile device configured to wirelessly transfer data to the pump assembly to cause the pump assembly to deliver the suggested medication bolus dosage to the user,
   wherein the mobile device is operable to prompt the user for confirmation of acceptance of a suggested medication bolus dosage to cause the pump assembly to deliver the suggested medication bolus dosage to the user, wherein confirmation of acceptance of the suggested medication bolus dosage by the user is provided by at least one of a security code or biometric validation.

2. The medical infusion pump system of claim 1, wherein the mobile device is a smartphone.

3. The medical infusion pump system of claim 1, further comprising:
   an accelerometer wherein movement information from the accelerometer is used by the controller device to verify detection of a bump between the pump assembly and the mobile device.

4. The medical infusion pump system of claim 1, further comprising:
   a glucose monitoring device configured to communicate to the controller a blood glucose level of the user.

5. The medical infusion pump system of claim 1, wherein the dosage calculator application takes into account previously delivered insulin that has not acted on the user.

6. The medical infusion pump system of claim 1, wherein the dosage calculator application is operable to:
   in response to a rejection of the suggested medication bolus dosage, provide the user with an option to modify the medication bolus dosage to an amount different from the suggested medication bolus dosage.

7. The medical infusion pump system of claim 1, wherein the pump device is a disposable component of the pump assembly and the controller device is a reusable component.

8. The medical infusion pump system of claim 1, wherein the pump device comprises:
one or more anchors that penetrate and retain the fluid cartridge inserted in the pump device to prevent removal of the fluid cartridge.

9. The medical infusion pump system of claim 1, wherein the pump device comprises:
a cap device that covers the fluid cartridge, wherein the cap device is non-reversibly attached to the first housing.

10. The medical infusion pump system of claim 1, wherein:
the first housing has a number of features that mate with complementary features of the second housing, wherein the second housing of the controller device is operable to removably attach with the pump device in a generally side-by-side configuration.

11. The medical infusion pump system of claim 1, further comprising:
a tube extending from the pump assembly to an infusion location.

12. The medical infusion pump system of claim 1, wherein the pump assembly is operable to:
provide a confirmation signal of bolus delivery.

13. The medical infusion pump system of claim 1, wherein the pump assembly is operable to:
receive data indicative of food consumption prior to determining suggested bolus dosage.

14. The medical infusion pump system of claim 1, wherein the wirelessly transferred data is a confirmation signal.

15. A medical infusion pump system, comprising:
a pump assembly that includes a pump device and a controller device, wherein the pump device is operable to receive a fluid cartridge and is in a first housing, the controller device is operable to control the pump device and is in a second housing, and the first housing and the second housing are configured to slidably engage one another; and
a mobile device comprising a memory for storing computer-readable instructions to access a dosage calculator application for calculating a suggested medication bolus dosage, the mobile device configured to wirelessly transfer data to the pump assembly to cause the pump assembly to deliver the suggested medication bolus dosage to the user, wherein the mobile device is operable to prompt the user for confirmation of acceptance of a suggested medication bolus dosage to cause the pump assembly to deliver the suggested medication bolus dosage to the user, wherein the confirmation of acceptance of the suggested medication bolus dosage by the user is provided by physically bumping the mobile device against the pump assembly.

16. A medical infusion pump system, comprising:
a pump assembly that includes a pump device, wherein the pump device is operable to receive a fluid cartridge;
a controller device, wherein the controller device is operable to control the pump device; and
a mobile device comprising a user interface, and a memory for storing computer-readable instructions to access a dosage calculator application for calculating a suggested medication bolus dosage, the mobile device operable to:
wirelessly transfer data to the pump assembly to cause the pump assembly to deliver the suggested medication bolus dosage to the user, and
prompt the user for confirmation of acceptance of a suggested medication bolus dosage to cause the pump assembly to deliver the suggested medication bolus dosage to the user, wherein confirmation of acceptance of the suggested medication bolus dosage by the user is provided via the user interface by at least one of a security code or biometric validation.

17. The medical infusion pump system of claim 16, wherein the controller device is incorporated in the mobile device or is incorporated with the pump assembly.

18. The medical infusion pump system of claim 16, further comprising:
a glucose monitoring device operable to communicate with the mobile device, wherein the controller device is incorporated in the mobile device or is incorporated with the pump assembly.

19. The medical infusion pump system of claim 16, wherein the biometric validation is performed via a fingerprint scan.

20. The medical infusion pump system of claim 16, wherein the biometric validation is performed via facial recognition.

* * * * *